United States Patent [19]

Meade et al.

[11] Patent Number: 5,707,605
[45] Date of Patent: Jan. 13, 1998

[54] MAGNETIC RESONANCE IMAGING AGENTS FOR THE DETECTION OF PHYSIOLOGICAL AGENTS

[75] Inventors: Thomas Meade, Altadena; Scott Fraser, Newport Beach; Russell Jacobs, Arcadia, all of Calif.

[73] Assignee: Research Corporation Technologies, Tucson, Ariz.

[21] Appl. No.: 486,968

[22] Filed: Jun. 7, 1995

Related U.S. Application Data

[63] Continuation of Ser. No. 460,511, Jun. 2, 1995, abandoned.
[51] Int. Cl.$^6$ .......................... A61K 49/00; G01N 31/00; G01N 33/48
[52] U.S. Cl. .......................... 424/9.35; 424/9.3; 424/9.323
[58] Field of Search .................. 424/1.11, 1.65, 424/1.69, 1.73, 9.1, 9.3, 9.32, 9.323, 9.34, 9.341, 9.5, 9.36, 9.361, 9.37; 534/10–16; 530/300, 324–330

[56] References Cited

U.S. PATENT DOCUMENTS

| | | | |
|---|---|---|---|
| 4,822,594 | 4/1989 | Gibby | 424/1.11 |
| 4,885,363 | 12/1989 | Tweedle et al. | 540/465 |
| 5,087,440 | 2/1992 | Cacheris et al. | 424/9 |
| 5,155,215 | 10/1992 | Ranney | 534/16 |
| 5,188,816 | 2/1993 | Sherry et al. | 424/9 |
| 5,219,553 | 6/1993 | Kraft et al. | 424/9 |
| 5,262,532 | 11/1993 | Tweedle et al. | 540/145 |
| 5,322,681 | 6/1994 | Klaveness | 424/9.1 |
| 5,358,704 | 10/1994 | Desreux et al. | 424/9 |
| 5,407,657 | 4/1995 | Unger et al. | 424/9.1 |
| 5,419,893 | 5/1995 | Berg et al. | 424/9.363 |
| 5,446,145 | 8/1995 | Love et al. | 540/465 |
| 5,466,439 | 11/1995 | Gibby et al. | 424/9.365 |
| 5,531,978 | 7/1996 | Berg et al. | 424/1.11 |
| 5,554,748 | 9/1996 | Sieving et al. | 540/465 |

FOREIGN PATENT DOCUMENTS

92/19264  5/1992  WIPO.

OTHER PUBLICATIONS

Meade, T.J. et al., "Hydrophobic, Regiospecific Guest Binding by Transition–Metal Host Complexes Having Permanent Voids as Revealed by FT–NMR Relaxation Studies," *J. Am. Chem. Soc.*, 108:1954–1962 (1986).

Meyer et al., "Advances in Macrocyclic Gadolinium Complexes as Magnetic Resonance Imaging Contrast Agents," *Investigative Radiology*, 25(1):S53–S55 (Sep. 1990).

Jackels, "Section III: Enhancement Agents for Magnetic Resonance and Ultrasound Imaging. Chapter 20: Enhancement Agents for Magnetic Resonance Imaging: Fundamentals," *Pharm. Med. Imag. Section III*, Chap. 20, pp. 645–661 (1990).

Alexander, "Design and Synthesis of Macrocyclic Ligands and Their Complexes of Lanthanides and Antinides," *Chem. Review*, 95:273–342 (1995).

*Primary Examiner*—John Kight
*Assistant Examiner*—Dameron L. Jones
*Attorney, Agent, or Firm*—Flehr Hohbach Test Albritton & Herbert LLP; Richard F. Trecartin; Robin M. Silva

[57] ABSTRACT

The invention relates to magnetic resonance imaging agents comprising a paramagnetic metal ion bound to a complex wherein said complex comprises a chelator and a blocking moiety convalently attached to said chelator which binds in at least a first coordination site of said metal ion and which is capable of interacting with a target substance such that the exchange of water in at least said first coordination site is increased.

16 Claims, 7 Drawing Sheets

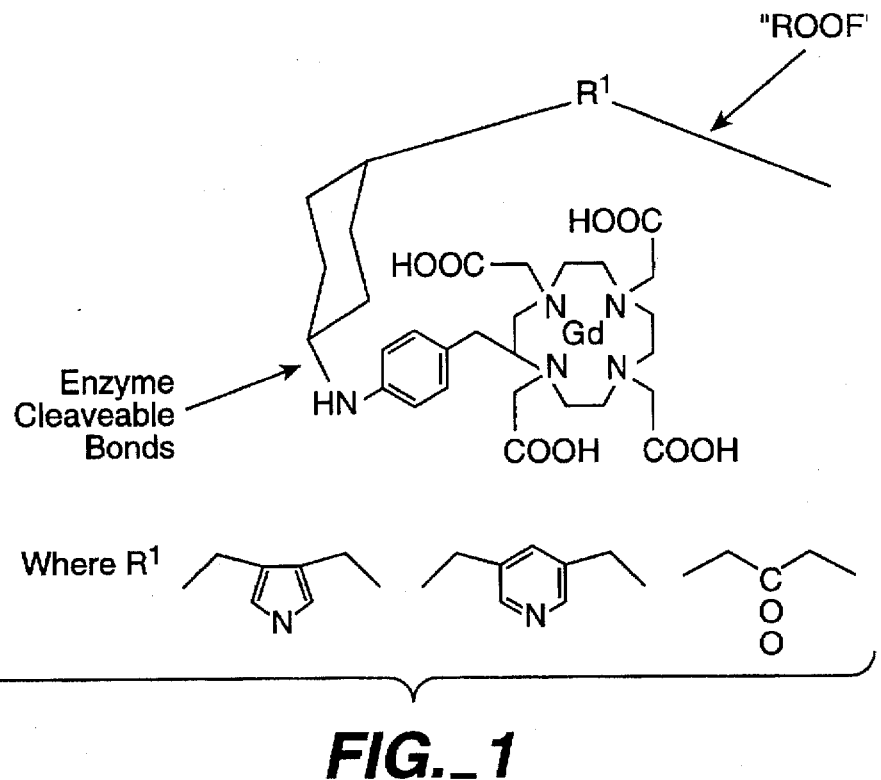
FIG._1
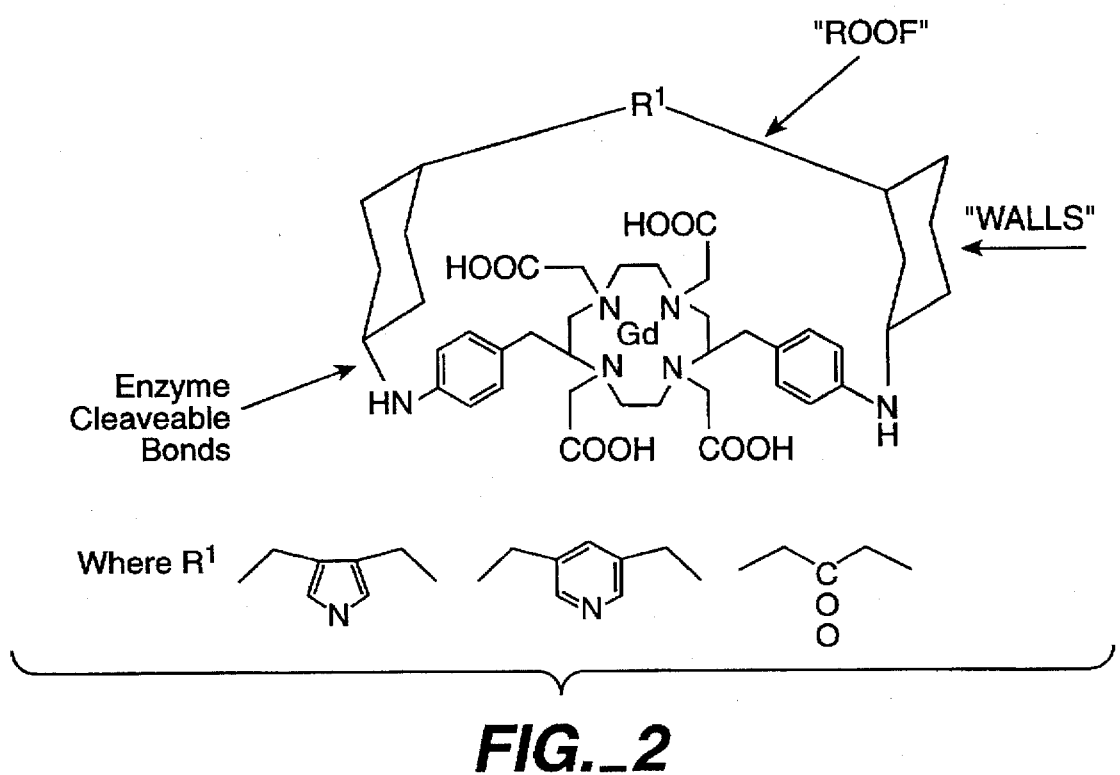
FIG._2

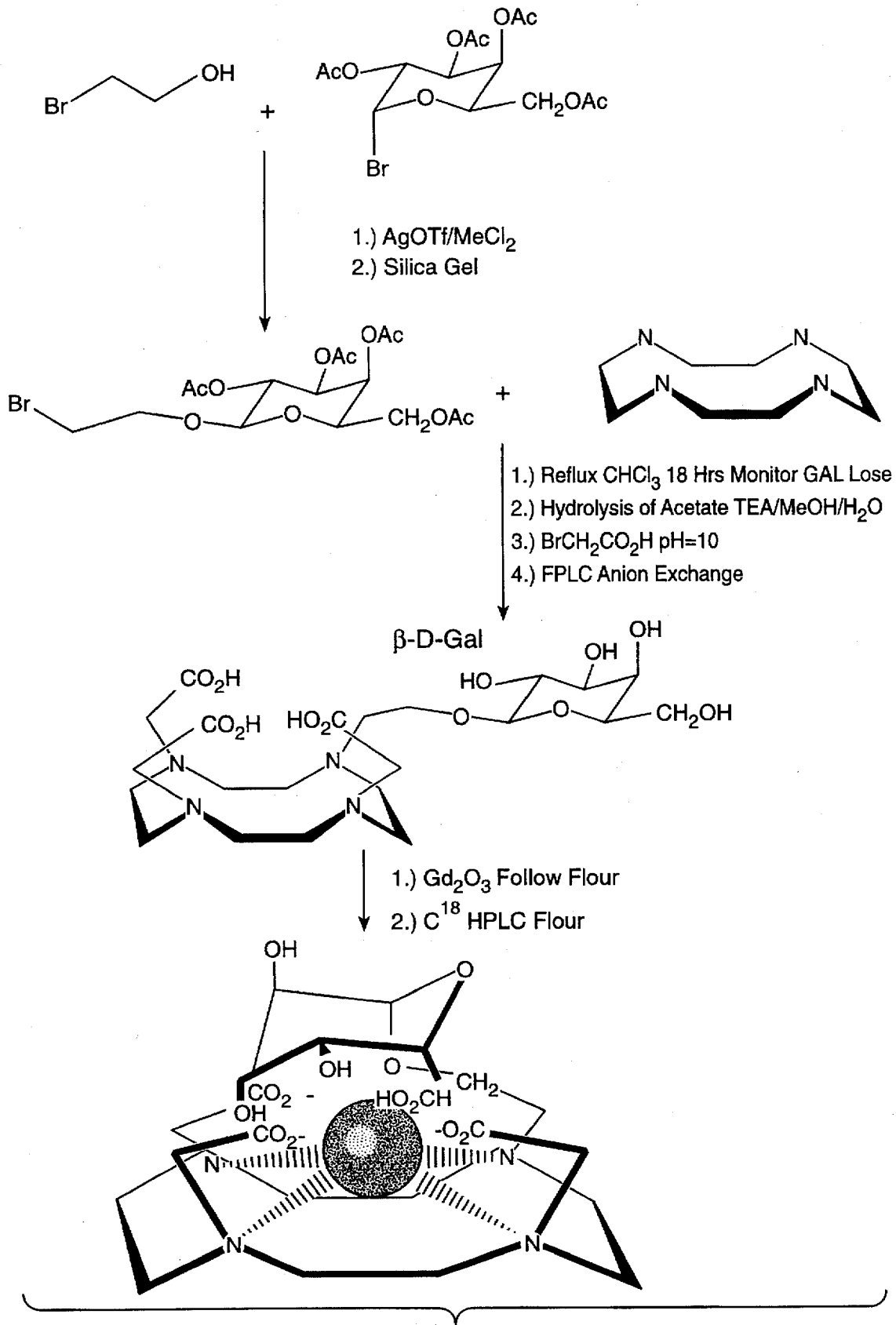
FIG._3

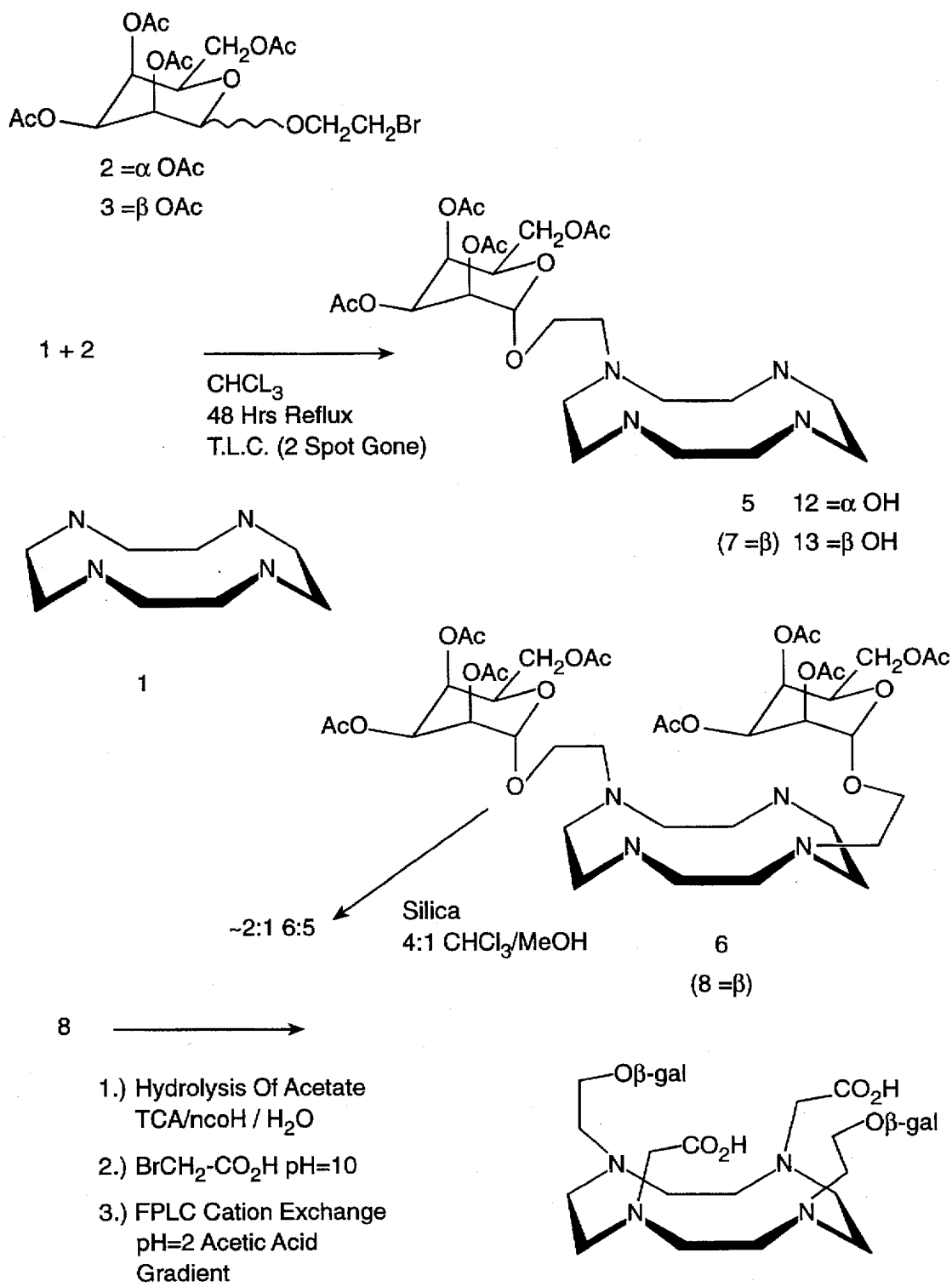
FIG._4

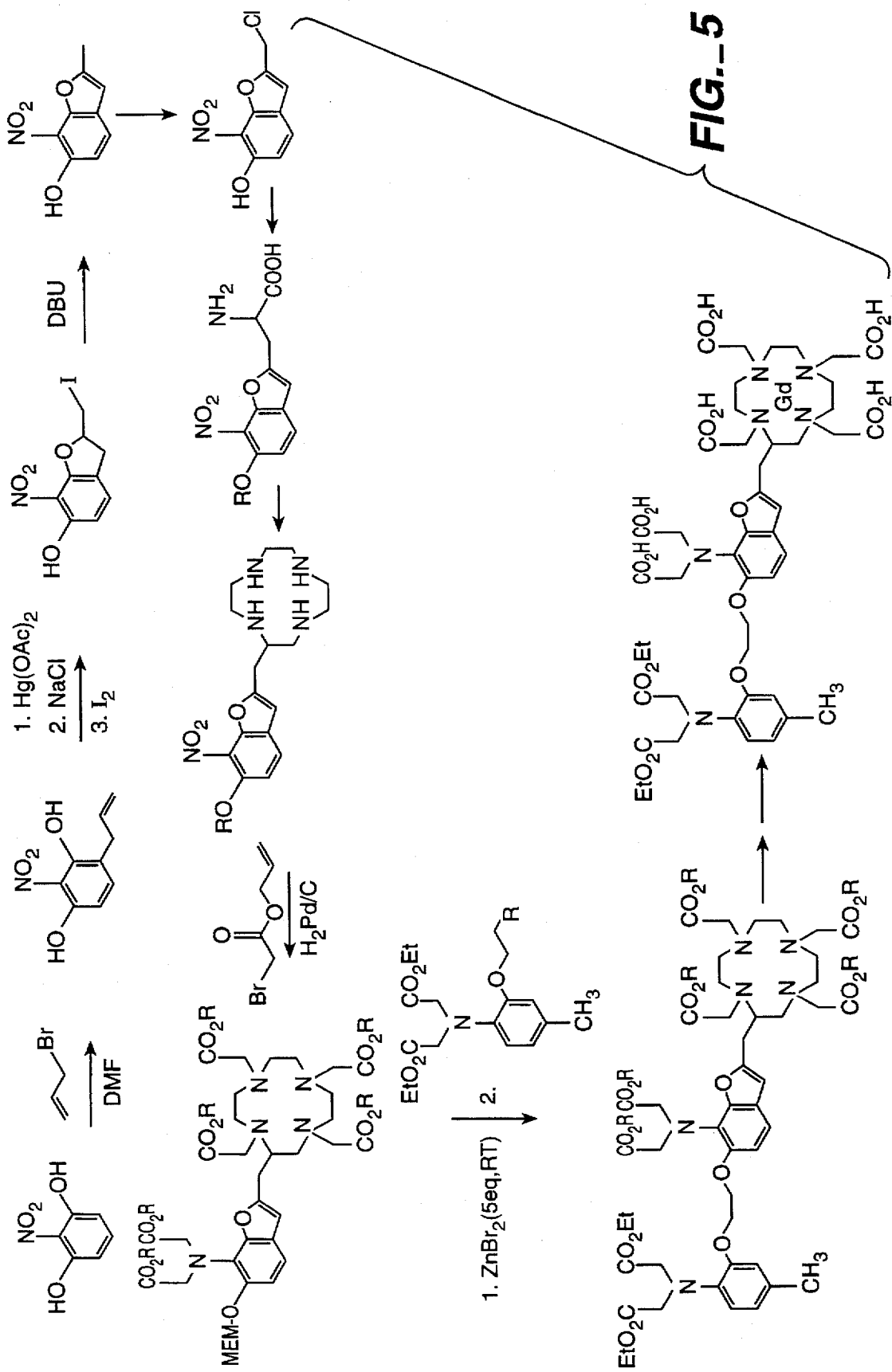
FIG._5

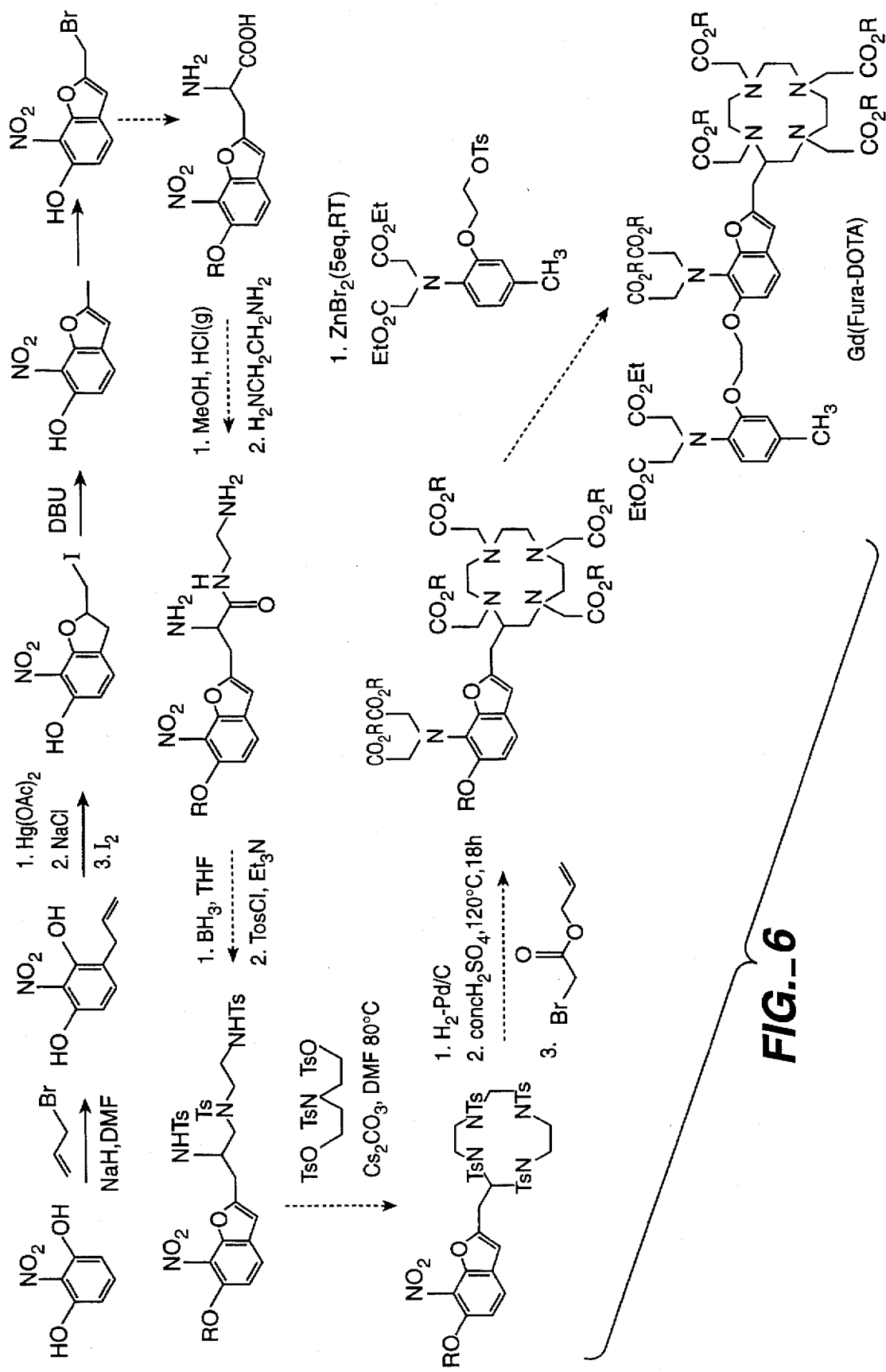
FIG._6

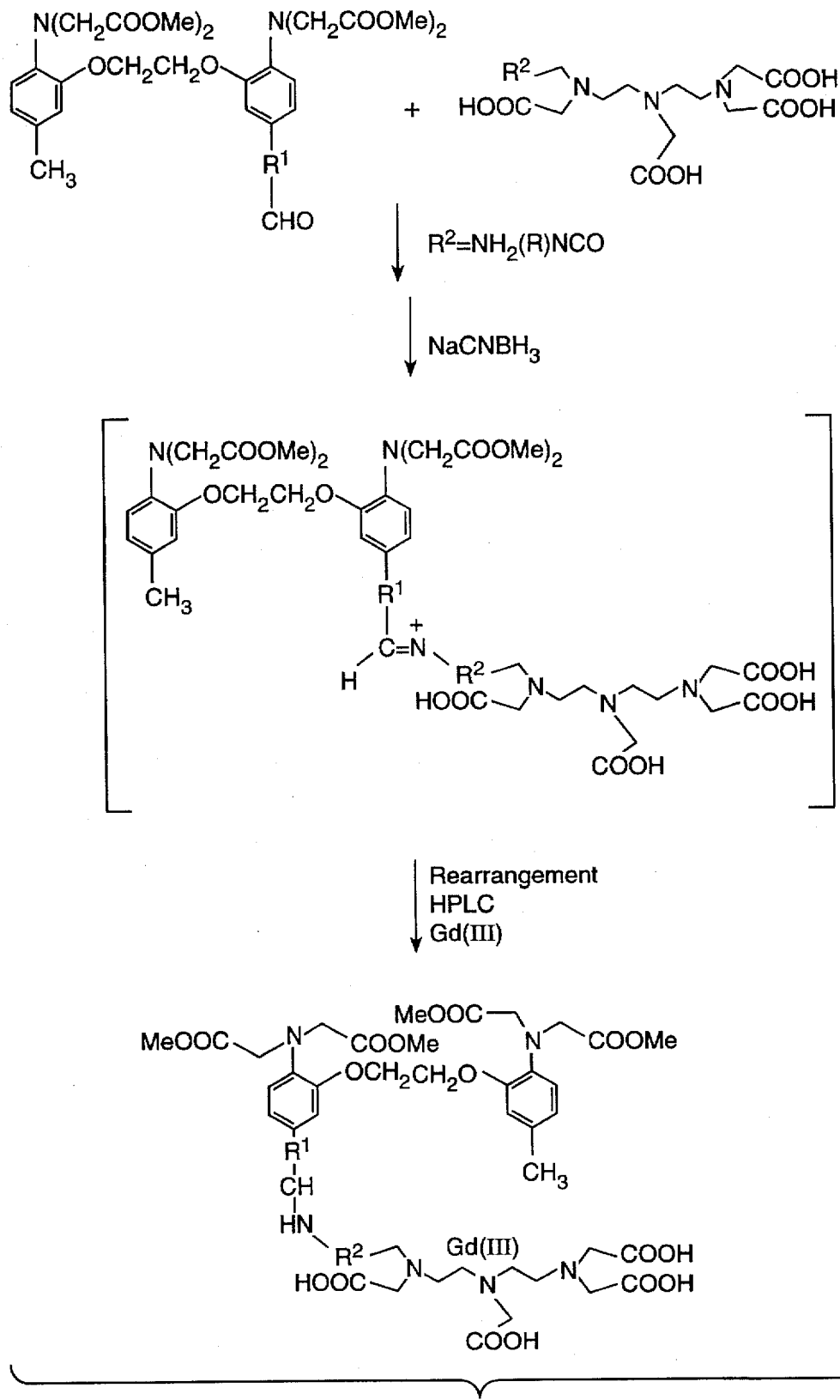
FIG._7

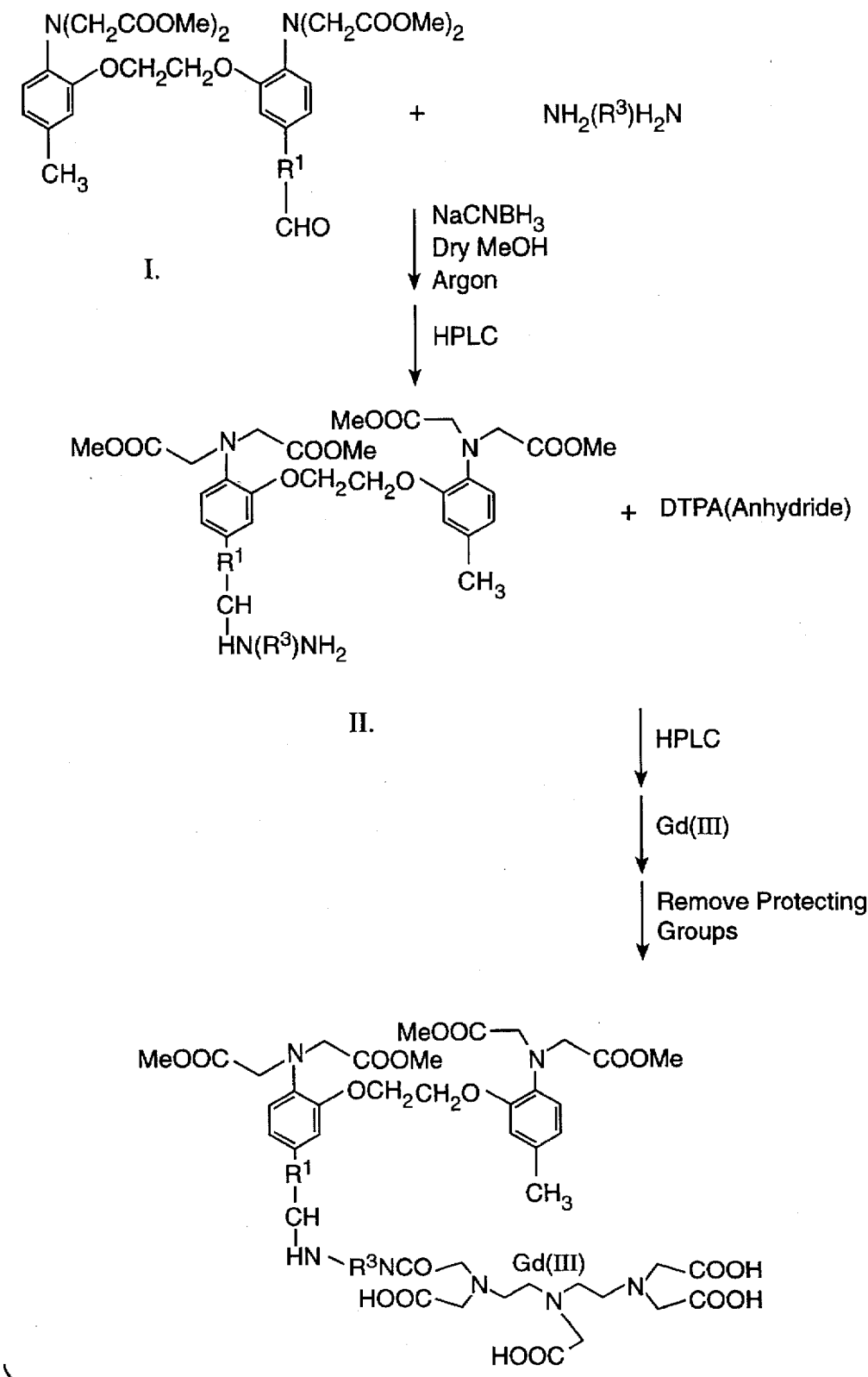
FIG._8

MAGNETIC RESONANCE IMAGING AGENTS FOR THE DETECTION OF PHYSIOLOGICAL AGENTS

This is a continuing application of U.S. Ser. No. 08/460, 511, filed Jun. 2, 1995, abandoned.

FIELD OF THE INVENTION

The invention relates to novel magnetic resonance imaging contrast agents and methods of detecting physiological signals or substances.

BACKGROUND OF THE INVENTION

Magnetic resonance imaging (MRI) is a diagnostic and research procedure that uses a large, high-strength magnet and radio-frequency signals to produce images. The most abundant molecular species in biological tissues is water. It is the quantum mechanical "spin" of the water proton nuclei that ultimately gives rise to the signal in all imaging experiments. In MRI the sample to be imaged is placed in a strong static magnetic field (1-12 Tesla) and the spins are excited with a pulse of radio frequency (RF) radiation to produce a net magnetization in the sample. Various magnetic field gradients and other RF pulses then act on the spins to code spatial information into the recorded signals. MRI is able to generate structural information in three dimensions in relatively short time spans.

Magnetic resonance (MR) images are typically displayed on a gray scale with black the lowest and white the highest measured intensity (I). This measured intensity is determined from the formula I=C*M, where C is the concentration of spins (in this case water concentration) and M is a measure of the magnetization present at time of the measurement. Although variations in water concentration (C) can give rise to contrast in MR images, it is the strong dependence of the rate of change of M on local environment that is the major source of image intensity variation in MRI. Two characteristic relaxation times are involved. $T_1$ is defined as the longitudinal relaxation time or spin lattice relaxation time ($1/T_1$ is a rate constant). $T_2$ is known as the transverse relaxation time or spin-spin mechanism, which is one of several contributions to $T_2$ ($1/T_2$ is also a rate constant). $T_1$ and $T_2$ have reciprocal effects on image intensity, with image intensity increased by either shortening the $T_1$ or lengthening the $T_2$.

In order to increase the signal-to-noise ratio (SNR) a typical MR imaging scan (RF and gradient pulse sequence and data acquisition) is repeated at a constant rate for a predetermined number of times and the data averaged. The signal amplitude recorded for any given scan is proportional to the number of spins that have decayed back to equilibrium since the previous scan. Thus, regions with rapidly decaying spins (i.e. short $T_1$ values) will recover all of their signal amplitude between successive scans. Their measured intensities in the final image will accurately reflect their spin density (i.e. water content). Regions with long $T_1$ values compared to the time between scans will progressively lose signal until a steady state condition is reached and will appear as darker regions in the final image. In extreme situations the linewidth can be so large that the signal is indistinguishable from background noise. In clinical imaging, water relaxation characteristics vary from tissue to tissue, providing the contrast which allows the discrimination of tissue types. Moreover, the MRI experiment can be setup so that regions of the sample with short $T_1$ values and/or long $T_2$ values are preferentially enhanced—so called $T_1$-weighted and $T_2$-weighted imaging protocols.

There is rapidly growing body of literature demonstrating the clinical effectiveness of paramagnetic contrast agents; currently there are at least eight different contrast agents in clinical trials or in use. Paramagnetic contrast agents serve to reduce $T_1$ and/or $T_2$. The capacity to differentiate regions or tissues that may be magnetically similar but histologically different is a major impetus for the preparation of these agents. These agents provide further contrast, and thus enhanced images, wherever the contrast agent is found. For example, the approved contrast agents outlined below may be injected into the circulatory system and used to visualize vascular structures and abnormalities, amongst other things.

In the design of MRI agents, strict attention must be given to a variety of properties that will ultimately effect the physiological outcome apart from the ability to provide contrast enhancement. Two fundamental properties that must be considered are biocompatability and proton relaxation enhancement. Biocompatibility is influenced by several factors including toxicity, stability (thermodynamic and kinetic), pharmacokinetics and biodistribution. Proton relaxation enhancement (or relaxivity) is chiefly governed by the choice of metal, the rotational correlation times and the accessibility of the metal to surrounding water molecules (rapid exchange of water with the bulk).

The measured relaxivity of the contrast agent is dominated by the selection of the metal atom. Paramagnetic metal ions, as a result of their unpaired electrons, act as potent relaxation enhancement agents. They decrease the $T_1$ relaxation times of nearby ($r^6$ dependence) spins. Some paramagnetic ions decrease the $T_1$ without causing substantial linebroadening (e.g. gadolinium (III), ($Gd^{3+}$)), while others induce drastic linebroadening (e.g. superparamagnetic iron oxide). The mechanism of $T_1$ relaxation is generally a through space dipole-dipole interaction between the unpaired electrons of the paramagnet (the metal atom with an unpaired electron) and bulk water molecules (those water molecules not "bound" to the metal atom) that are in fast exchange with water molecules in the metal's inner coordination sphere (those water molecules bound to the metal atom).

The shortening of proton relaxation times by Gd is mediated by dipole-dipole interactions between its unpaired electrons and adjacent water protons. The effectiveness of Gd's magnetic dipole drops off very rapidly as a function of its distance from these protons. Consequently, the protons which are relaxed most efficiently are those which are able to enter Gd's first or second coordination spheres during the interval between the RF pulse and signal detection. For example, regions associated with a Gd(III) ion (near-by water molecules) appear bright in an MR image where the normal aqueous solution appears as dark background if the time between successive scans in the experiment is short (i.e. $T_1$ weighted image).

Localized $T_2$ shortening caused by superparamagnetic particles is believed to be due to the local magnetic field inhomogeneities associated with the large magnetic moments of these particles. Regions associated with a superparamagnetic iron oxide particle appear dark in an MR image where the normal aqueous solution appears as high intensity background if the echo time (TE) in the spin-echo pulse sequence experiment is long (i.e. $T_2$-weighted image).

The lanthanide atom Gd(III), has generally been chosen as the metal atom for contrast agents because it has a high magnetic moment ($\mu^2=63BM^2$), a symmetric electronic ground state, ($S^8$), the largest paramagnetic dipole and the greatest paramagnetic relaxivity of any element. Gd(III) has been chelated with several substances to render the complex nontoxic. To date, a number of chelators have been used, including diethylenetriaminepentaacetic (DTPA), 1,4,7,10-tetraazacyclododecane'-N,N'N",N'''-tetracetic acid (DOTA), and derivatives thereof. See U.S. Pat. Nos. 5,155,215, 5,087,440, 5,219,553, 5,188,816, 4,885,363, 5,358,704, 5,262,532, and Meyer et al., Invest. Radiol. 25:S53 (1990).

The stability constant (K) for Gd(DTPA) is very high (logK=22.4) and is more commonly known as the formation constant (the higher the logK, the more stable the complex). This thermodynamic parameter indicates the fraction of Gd(III) ions that are in the unbound state will be quite small and should not be confused with the rate (kinetic stability) at which the loss of metal occurs. The water soluble Gd(DTPA)-chelate is stable, nontoxic, and one of the most widely used contrast enhancement agents in experimental and clinical imaging research. It was approved for clinical use in adult patients in June of 1988. It is an extracellular agent that accumulates in tissue by perfusion dominated processes. Image enhancement improvements using Gd(DTPA) are well documented in a number of applications (Runge et al., Magn. Reson. Imag. 3:85 (1991); Russell et al., AJR 152:813 (1989); Meyer et al., Invest. Radiol. 25:S53 (1990)) including visualizing blood-brain barrier disruptions caused by space occupying lesions and detection of abnormal vascularity. It has recently been applied to the functional mapping of the human visual cortex by defining regional cerebral hemodynamics (Belliveau et al., (1991) 254:719).

Another chelator used in Gd contrast agents is the macrocyclic ligand 1,4,7,10-tetraazacyclododecane-N,N',N'',N'''-tetracetic acid (DOTA). The Gd-DOTA complex has been thoroughly studied in laboratory tests involving animals and humans. The complex is conformationally rigid, has an extremely high formation constant (logK=28.5), and at physiological pH possess very slow dissociation kinetics. Recently, the GdDOTA complex was approved as an MRI contrast agent for use in adults and infants in France and has been administered to over 4500 patients.

As noted above, these MRI contrast agents have a variety of uses. However, there are no contrast agents which allow the visualization of specific components within a biological or other type of sample. Accordingly, it is an object of the present invention to provide MRI contrast or enhancement agents which allow the visualization and detection of physiological agents within an animal, tissue or cells.

SUMMARY OF THE INVENTION

In accordance with the above objects, the invention provides MRI agents comprising a paramagnetic metal ion bound to a complex. The complex comprises a chelator and a blocking moiety in at least a first coordination site of said metal ion. The blocking moiety is covalently attached to the chelator, and capable of interacting with a target substance such that the exchange of water in at least said first coordination site in the metal ion complex is altered.

The invention further provides MRI agents comprising a paramagnetic metal ion capable of binding n coordination atoms. The metal ion is bound to a chelator such that said metal ion has coordination atoms at (n-1 or n-2) coordination sites of said metal ion. The MRI agent further comprises a blocking moiety which hinders the rapid exchange of water in the remaining coordination site or sites, and which is capable of interacting with a target substance, such that the exchange of water at the remaining coordination site or sites is increased.

The invention further comprises a MRI agent comprising a Gd(III) ion with coordination atoms at 8 coordination sites of the Gd(III) ion. The MRI agent further comprises a blocking moiety which hinders the rapid exchange of water in a 9th coordination site, which is capable of interacting with a target substance, such that the exchange of water at the 9th coordination site is increased.

The invention further provides MRI agents comprising a composition having the formula:

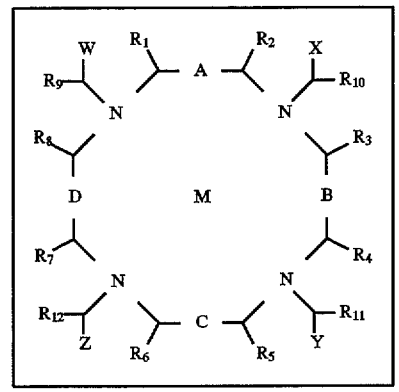

In this structure, M is a paramagnetic metal ion selected from the group consisting of Gd(III), Fe(III), Mn(II), Yt(III), Cr(III) and Dy(III). A, B, C and D are either single bonds or double bonds. W, X, Y and Z are —OH, —COO—, —CH$_2$OH or —CH$_2$COO—. $R_1$–$R_{12}$ are alkyl, substituted alkyl, a phosphorus moiety or a blocking moiety, and at least one of $R_1$–$R_{12}$ is a blocking moiety.

The invention also provides MRI agents having the formula:

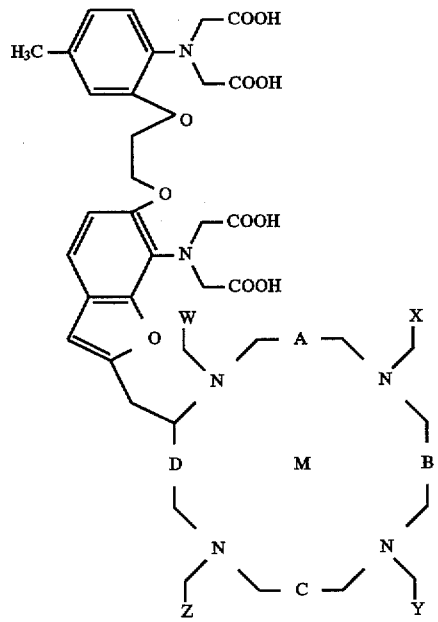

In this structure, M is a paramagnetic metal ion selected from the group consisting of Gd(III), Fe(III), Mn(II), Yt(III), Cr(III) and Dy(III). A, B, C and D are either single bonds or double bonds. W, X, Y and Z are —OH, —COO—, —CH$_2$OH or —CH$_2$COO—, and R$_1$–R$_{12}$ are alkyl, substituted alkyl, or a phosphorus moiety.

The invention further provides MRI agents having the formula:

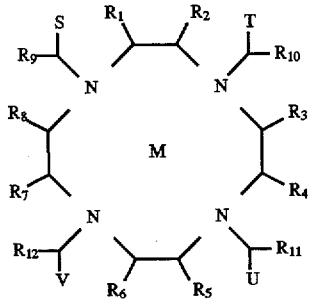

In this structure, M is a paramagnetic metal ion selected from the group consisting of Gd(III), Fe(III), Mn(II), Yt(III), Cr(III) and Dy(III). A, B, C, and D are either single or double bonds. S, T, U and V are —OH, —COO—, —CH2OH, —CH2COO—, or a blocking moiety, and R$_1$–R$_{12}$ are alkyl, substituted alkyl, or a phosphorus moiety. Further, at least one of S, T, U or V is a blocking moiety.

The invention also provides MRI agents having the formula:

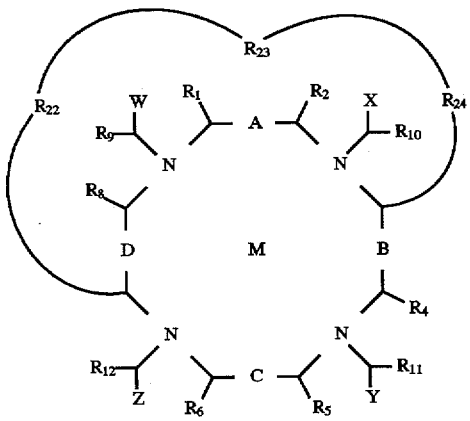

In this structure, M is a paramagnetic metal ion selected from the group consisting of Gd(III), Fe(III), Mn(II), Yt(III), Cr(III) and Dy(III). A, B, C and D are either single bonds or double bonds. W, X, Y and Z are —OH, —COO—, —CH$_2$OH or —CH$_2$COO—. R$_1$–R$_{12}$ are alkyl, substituted alkyl, a phosphorus moiety or a blocking moiety, and R$_{22}$, R$_{23}$ and R$_{24}$ comprise a blocking moiety, with R$_{23}$ being a coordination site barrier.

The invention further provides MRI agents having the formula:

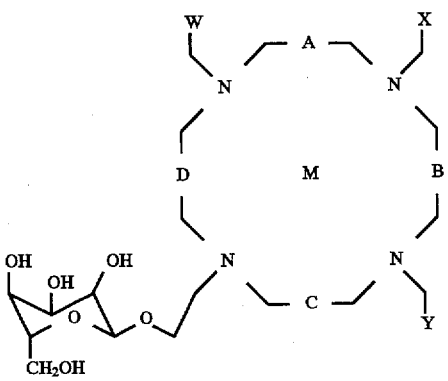

In this structure, M is a paramagnetic metal ion selected from the group consisting of Gd(III), Fe(III), Mn(II), Yt(III), Cr(III) and Dy(III). A, B, C and D are either single bonds or double bonds. W, X, and Y are —OH, —COO—, —CH$_2$OH or —CH$_2$COO—, and R$_1$–R$_{12}$ are alkyl, substituted alkyl, or phosphorus moiety.

Further provided are MRI agents having a formula comprising:

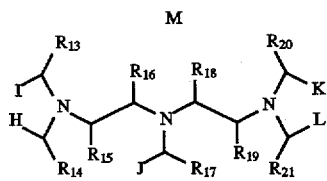

In this structure, M is a paramagnetic metal ion selected from the group consisting of Gd(III), Fe(III), Mn(II), Yt(III), Cr(III) and Dy(III). H, I, J, K and L are —OH, —COO—, —CH2OH, —CH2COO—, or a blocking moiety. R$_{13}$–R$_{21}$ are alkyl, substituted alkyl, a phosphorus moiety or a blocking moiety, and at least one of R$_{13}$–R$_{21}$, H, I, J, K or L is a blocking moiety.

The invention also provides methods of magnetic resonance imaging of a cell, tissue, experimental animal or patient comprising administering an MRI agent of the invention to a cell, tissue, experimental animal or patient and rendering a magnetic resonance image of said cell, tissue, experimental animal or patient.

BRIEF DESCRIPTION OF THE DRAWINGS

FIG. 1 depicts a representative complex of the invention, where the blocking moiety is tethered at one end only. The blocking moiety comprises a enzyme substrate and a coordination site barrier. The R group is the coordination site barrier.

FIG. 2 depicts a representative complex of the invention, wherein the blocking moiety is tethered at two ends. The R group is the coordination site barrier.

FIG. 3 depicts a representative synthesis of Do3a-hydroxyethyl-β-galactose, which has a single galactose moiety attached to the DOTA ring.

FIG. 4 depicts a representative synthesis of a β-galactose-DOTA derivative that has two galactose moieties attached to the DOTA ring.

FIG. 5 depicts the synthesis of a BAPTA-DOTA derivative.

FIG. 6 depicts the synthesis of a FURA-DOTA derivative.

FIG. 7 depicts a synthetic scheme for the synthesis of BAPTA-DTPA.

FIG. 8 depicts an alternative synthesis of a BAPTA-DTPA derivative.

DETAILED DESCRIPTION OF THE INVENTION

The present invention provides magnetic resonance imaging contrast agents which can detect physiological agents or target substances. The MRI agents of the invention are relatively inactive as contrast enhancement agents in the absence of the physiological target substance, and are activated, thus altering the MR image, in the presence of the physiological target substance.

Viewed simplistically, this "trigger" mechanism, whereby the contrast agent is "turned on" by the presence of the target substance, is based on a dynamic equilibrium that affects the rate of exchange of water molecules in one or more coordination sites of a paramagnetic metal ion contained in the MRI contrast agents of the present invention. In turn, the rate of exchange of the water molecule is determined by the presence or absence of the target substance in the surrounding environment. Thus, in the absence of the target substance, the metal ion complexes of the invention which chelate the paramagnetic ion have reduced coordination sites available which can rapidly exchange with the water molecules of the local environment. In such a situation, the coordination sites are substantially occupied or blocked by the coordination atoms of the chelator and at least one blocking moiety. Thus, the paramagnetic ion has essentially no water molecules in its "inner-coordination sphere", i.e. actually bound to the metal when the target substance is absent. It is the interaction of the paramagnetic metal ion with the protons on the inner coordination sphere water molecules and the rapid exchange of such water molecules that cause the high observed relaxivity, and thus the imaging effect, of the paramagnetic metal ion. Accordingly, if all the coordination sites of the metal ion in the metal ion complex are filled with moieties other than water molecules, as is the case when the target substance is absent, there is little if any net enhancement of the imaging signal by the metal ion complexes of the invention. However, when present, the target substance interacts with the blocking moiety or moieties of the metal ion complex, effectively freeing at least one of the inner-sphere coordination sites on the metal ion complex. The water molecules of the local environment are then available to occupy the inner-sphere coordination site or sites, which will cause an increase in the rate of exchange of water and relaxivity of the metal ion complex toward water thereby producing image enhancement which is a measure of the presence of the target substance.

Generally, a 2 to 5% change in the MRI signal used to generate the image is enough to be detectable. Thus, it is preferred that the agents of the invention in the presence of a target substance increase the MRI signal by at least 2 to 5% as compared to the signal gain the absence of the target substance. Signal enhancement of 2 to 15% is preferred, and 10 to 20% is more preferred for each coordination site made available by the target substance interaction with the blocking moiety. That is, when the blocking moiety occupies two or more coordination sites, the release of the blocking moiety can result in double the increase in signal or more as compared to a single coordination site.

It should be understood that even in the absence of the target substance, at any particular coordination site, there will be a dynamic equilibrium for one or more coordination sites as between a coordination atom of the blocking moiety and water molecules. That is, even when a coordination atom is tightly bound to the metal, there will be some exchange of water molecules at the site. However, in most instances, this exchange of water molecules is neither rapid nor significant, and does not result in significant image enhancement. However, upon exposure to the target substance, the blocking moiety dislodges from the coordination site and the exchange of water is increased, i.e. rapid exchange and therefore an increase in relaxivity may occur, with significant image enhancement.

The complexes of the invention comprise a chelator and a blocking moiety. The metal ion complexes of the invention comprise a paramagnetic metal ion bound to a complex comprising a chelator and a blocking moiety. By "paramagnetic metal ion", "paramagnetic ion" or "metal ion" herein is meant a metal ion which is magnetized parallel or antiparallel to a magnetic field to an extent proportional to the field. Generally, these are metal ions which have unpaired electrons; this is a term understood in the art. Examples of suitable paramagnetic metal ions, include, but are not limited to, gadolinium III (Gd+3 or Gd(III)), iron III (Fe+3 or Fe(III)), manganese II (Mn+2 or Mn(II)), yttrium III (Yt+3 or Yt(III)), dysprosium (Dy+3 or Dy(III)), and chromium (Cr(III) or Cr+3). In a preferred embodiment the paramagnetic ion is the lanthanide atom Gd(III), due to its high magnetic moment ($u^2$=63BM2), a symmetric electronic ground state (S8), and its current approval for diagnostic use in humans.

In addition to the metal ion, the metal ion complexes of the invention comprise a chelator and a blocking moiety which may be covalently attached to the chelator. Due to the relatively high toxicity of many of the paramagnetic ions, the ions are rendered nontoxic in physiological systems by binding to a suitable chelator. Thus, the substitution of blocking moieties in coordination sites of the chelator, which in the presence of the target substance are capable of vacating the coordination sites in favor of water molecules, may render the metal ion complex more toxic by decreasing the half-life of dissociation for the metal ion complex. Thus, in a preferred embodiment, only a single coordination site is occupied or blocked by a blocking moiety. However, for some applications, e.g. analysis of tissue and the like, the toxicity of the metal ion complexes may not be of paramount importance. Similarly, some metal ion complexes are so stable that even the replacement of one or more additional coordination atoms with a blocking moiety does not significantly effect the half-life of dissociation. For example, DOTA, described below, when complexed with Gd(III) is extremely stable. Accordingly, when DOTA serves as the chelator, several of the coordination atoms of the chelator may be replaced with blocking moieties without a significant increase in toxicity. Additionally such an agent would potentially produce a larger signal since it has two or more coordination sites which are rapidly exchanging water with the bulk solvent.

There are a variety of factors which influence the choice and stability of the chelate metal ion complex, including enthalpy and entropy effects (e.g. number, charge and basicity of coordinating groups, ligand field and conformational effects).

In general, the chelator has a number of coordination sites containing coordination atoms which bind the metal ion. The number of coordination sites, and thus the structure of the chelator, depends on the metal ion. The chelators used in the metal ion complexes of the present invention preferably have at least one less coordination atom (n-1) than the metal ion is capable of binding (n), since at least one coordination site of the metal ion complex is occupied or blocked by a blocking moiety, as described below, to confer functionality on the metal ion complex. Thus, for example, Gd(III) may have 8 strongly associated coordination atoms or ligands and is capable of weakly binding a ninth ligand. Accordingly, suitable chelators for Gd(III) will have less than 9 coordination atoms. In a preferred embodiment, a Gd(III) chelator will have 8 coordination atoms, with a blocking moiety either occupying or blocking the remaining site in the metal ion complex. In an alternative embodiment, the chelators used in the metal ion complexes of the invention have two less coordination atoms (n-2) than the metal ion is capable of binding (n), with these coordination sites occupied by one or more blocking moieties. Thus, alternative embodiments utilize Gd(III) chelators with 6 or 7 coordination atoms, with the blocking moiety either occupying or blocking the remaining sites. It should be appreciated that the exact structure of the chelator and blocking moiety may be difficult to determine, and thus the exact number of coordination atoms may be unclear. For example, it is possible that the chelator provide 7.5 coordination atoms, i.e. the 8th coordination atom is on average not fully bound to the metal ion. However, the metal ion complex may still be functional, if the 8th coordination atom is sufficiently bound to prevent the rapid exchange of water at the site, and/or the blocking moiety impedes the rapid exchange of water at the site.

There are a large number of known macrocyclic chelators or ligands which are used to chelate lanthanide and paramagnetic ions. See for example, Alexander, Chem. Rev. 95:273-342 (1995) and Jackels, Pharm. Med. Imag, Section III, Chap. 20, p645 (1990), expressly incorporated herein by reference, which describes a large number of macrocyclic chelators and their synthesis. Similarly, there are a number of patents which describe suitable chelators for use in the invention, including U.S. Pat. Nos. 5,155,215, 5,087,440, 5,219,553, 5,188,816, 4,885,363, 5,358,704, 5,262,532, and Meyer et al., Invest. Radiol. 25:S53 (1990), all of which are also expressly incorporated by reference. Thus, as will be understood by those in the art, any of the known paramagnetic metal ion chelators or lanthanide chelators can be easily modified using the teachings herein to further comprise at least one blocking moiety.

When the metal ion is Gd(III), a preferred chelator is 1,4,7,10-tetraazacyclododecane-N,N',N", N'"-tetracetic acid (DOTA) or substituted DOTA. DOTA has the structure shown below:

Structure 1

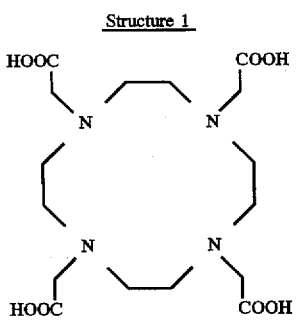

By "substituted DOTA" herein is meant that the DOTA may be substituted at any of the following positions, as shown below:

Structure 2

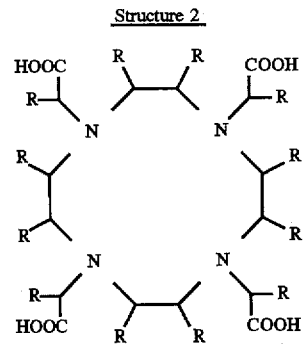

Suitable R substitution groups include a wide variety of groups, as will be understood by those in the art. For example, suitable substitution groups include substitution groups disclosed for DOTA and DOTA-type compounds in U.S. Pat. Nos. 5,262,532, 4,885,363, and 5,358,704. These groups include hydrogen, alkyl groups, substituted alkyl groups, phosphorus moieties, and blocking moieties. As will be appreciated by those skilled in the art, each position designated above may have two R groups attached (R' and R"), although in a preferred embodiment only a single R group is attached at any particular position, and in further preferred embodiments all but one of the R groups is hydrogen, with the remaining group comprising a blocking moiety.

By "alkyl group" or grammatical equivalents herein is meant a straight or branched chain alkyl group, with straight chain alkyl groups being preferred. If branched, it may be branched at one or more positions, and unless specified, at any position. Also included within the definition of an alkyl group are cycloalkyl groups such as C5 and C6 rings, aromatic aryl rings such as phenyl, heterocyclic aromatic rings such as pyridine, furan, thiophene, pyrrole, indole and purine, and heterocyclic rings with nitrogen, oxygen, sulfur or phosphorus. Additional suitable heterocyclic substituted rings are depicted in U.S. Pat. No. 5,087,440, expressly incorporated by reference. In some embodiments, two adjacent R groups may be bonded together to form ring structures together with the carbon atoms of the chelator, such as is described in U.S. Pat. No. 5,358,704, expressly incorporated by reference. These ring structures may be similarly substituted.

The alkyl group may be substituted, with one or more substitution groups. For example, a phenyl group may be a substituted phenyl group. Suitable substitution groups include, but are not limited to, halogens such as chlorine, bromine and fluorine, amines, hydroxy groups, carboxylic acids, nitro groups, carbonyl and other alkyl and aryl groups. Thus, arylalkyl and hydroxyalkyl groups are also suitable for use in the invention. Preferred substitution groups include alkyl amines and alkyl hydroxy.

The alkyl group may range from about 1 to 20 carbon atoms (C1–C20), with a preferred embodiment utilizing from about 1 to about 10 carbon atoms (C1–C10), with about C1 through about C5 being preferred. However, in some embodiments, the alkyl group may be larger, for example when the alkyl group is the coordination site barrier.

By "alkyl amine" or grammatical equivalents herein is meant an alkyl group as defined above, substituted with an amine group at any position. In addition, the alkyl amine may have other substitution groups, as outlined above for alkyl group. The amine may be primary (—$NH_2R$), secondary (—$NHR_2$), or tertiary (—$NR_3$). When the amine is a secondary or tertiary amine, suitable R groups are alkyl groups as defined above. A preferred alkyl amine is p-aminobenzyl. When the alkyl amine serves as the coordination site barrier, as described below, preferred embodiments utilize the nitrogen atom of the amine as a coordination atom, for example when the alkyl amine includes a pyridine or pyrrole ring.

By "phosphorous moieties" herein is meant moieties containing the —$PO(OH)(R_{25})_2$ group. The phosphorus may be an alkyl phosphorus; for example, DOTEP utilizes ethylphosphorus as a substitution group on DOTA. $R_{25}$ may be alkyl, substituted alkyl, hydroxy. A preferred embodiment has a —$PO(OH)_2R_{25}$ group.

The substitution group may also be hydrogen or a blocking moiety, as is described below.

In an alternative embodiment, when the metal ion is Gd(III), a preferred chelator is diethylenetriaminepentaacetic acid (DTPA) or substituted DTPA. DPTA has the structure shown below:

Structure 3

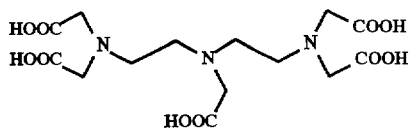

By "substituted DPTA" herein is meant that the DPTA may be substituted at any of the following positions, as shown below:

Structure 4

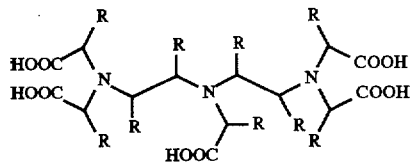

See for example U.S. Pat. No. 5,087,440.

Suitable R substitution groups include hydrogen, alkyl groups, alkyl amine groups, phosphorus moieties, and blocking moieties, all as defined above. Again, those skilled in the art will appreciate that there may be two R groups (R' and R") at each position designated above, although as described herein, preferably all but one of the R groups is hydrogen.

In an alternative embodiment, when the metal ion is Gd(III), a preferred chelator is 1,4,7,10-tetraazacyclododecane-N,N',N",N'''-tetraethylphosphorus (DOTEP) or substituted DOTEP (see U.S. Pat. No. 5,188, 816). DOTEP has the structure shown below:

Structure 5

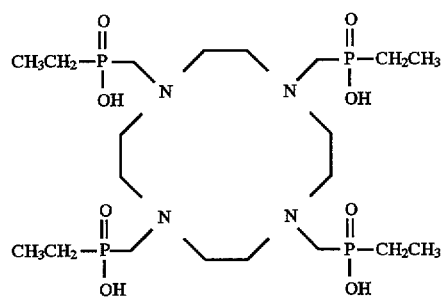

DOTEP may have similar R substitution groups as outlined above.

Other suitable Gd(III) chelators are described in Alexander, supra, Jackels, supra, U.S. Pat. Nos. 5,155,215, 5,087,440, 5,219,553, 5,188,816, 4,885,363, 5,358,704, 5,262,532, and Meyer et al., Invest. Radiol. 25:S53 (1990), among others.

When the paramagnetic ion is Fe(III), appropriate chelators will have less than 6 coordination atoms, since Fe(III) is capable of binding 6 coordination atoms. Suitable chelators for Fe(III) ions are well known in the art, see for example Lauffer et al., J. Am. Chem. Soc. 109:1622 (1987); Lauffer, Chem. Rev. 87:901–927 (1987); and U.S. Pat. Nos. 4,885,363, 5,358,704, and 5,262,532, all which describe chelators suitable for Fe(III).

When the paramagnetic ion is Mn(II) (Mn+2), appropriate chelators will have less than 5 or 6 coordination atoms, since Mn(II) is capable of binding 6 or 7 coordination atoms. Suitable chelators for Mn(II) ions are well known in the art; see for example Lauffer, Chem. Rev. 87:901–927 (1987) and U.S. Pat. Nos. 4,885,363, 5,358,704, and 5,262,532.

When the paramagnetic ion is Yt(III), appropriate chelators will have less than 7 or 8 coordination atoms, since Yt(III) is capable of binding 8 or 9 coordination atoms. Suitable chelators for Yt(III) ions include, but are not limited to, DOTA and DPTA and derivatives thereof (see Moi et al., J. Am. Chem. Soc. 110:6266–6267 (1988)) and those chelators described in U.S. Pat. No. 4,885,363 and others, as outlined above.

When the paramagnetic ion is Dy+3 (Dy(III)), appropriate chelators will have less than 7 or 8 coordination atoms, since DyIII is capable of binding 8 or 9 coordination atoms. Suitable chelators are known in the art, as above.

In a preferred embodiment, the chelator and the blocking moiety are covalently linked; that is, the blocking moiety is a substitution group on the chelator. In this embodiment, the substituted chelator, with the bound metal ion, comprises the metal ion complex which in the absence of the target substance has all possible coordination sites occupied or blocked; i.e. it is coordinatively saturated.

In an alternative embodiment, the chelator and the blocking moiety are not covalently attached. In this embodiment, the blocking moiety has sufficient affinity for the metal ion to prevent the rapid exchange of water molecules in the absence of the target substance. However, in this embodiment the blocking moiety has a higher affinity for the target substance than for the metal ion. Accordingly, in the presence of the target substance, the blocking moiety will have a tendency to be dislodged from the metal ion to interact with the target substance, thus freeing up a coordination site in the metal ion complex and allowing the rapid exchange of water and an increase in relaxivity.

What is important is that the metal ion complex, comprising the metal ion, the chelator and the blocking moiety, is not readily able to rapidly exchange water molecules when the blocking moieties are in the inner coordination sphere of the metal ion, such that in the absence of the target substance, there is less or little substantial image enhancement.

By "blocking moiety" or grammatical equivalents herein is meant a functional group associated with the chelator metal ion complexes of the invention which is capable of interacting with a target substance and which is capable, under certain circumstances, of substantially blocking the exchange of water in at least one inner coordination site of the metal ion of the metal ion complex. For example, when bound to or associated with the metal ion complexes of the invention, the blocking moiety occupies or blocks at least one coordination site of the metal ion in the absence of the target substance. Thus, the metal ion is coordinately saturated with the chelator and the blocking moiety or moieties in the absence of the target substance.

A blocking moiety may comprise several components. The blocking moiety has a functional moiety which is capable of interacting with a target substance, as outlined below. This functional moiety may or may not provide the coordination atom(s) of the blocking moiety. In addition, blocking moieties may comprise one or more linker groups to allow for correct spacing and attachment of the components of the blocking moiety. Furthermore, in the embodiment where the functional group of the blocking moiety does not contribute a coordination atom, the blocking moiety may comprise a coordination site barrier, which serves to either provide a coordination site atom or sterically prevent the rapid exchange of water at the coordination site; i.e. the coordination site barrier may either occupy or block the coordination site.

By "capable of interacting with a target substance" herein is meant that the blocking moiety has an affinity for the target substance, such that the blocking moiety will stop blocking or occupying at least one coordination site of the metal ion complex when the target substance is present. Thus, as outlined above, the blocking moiety is blocking or occupying at least one coordination site of the metal ion in the absence of the target substance. However, in the presence of the target substance, the blocking moiety associates or interacts with the target substance and is released from its association with the metal ion, thus freeing at least one coordination site of the metal ion such that the rapid exchange of water can occur at this site, resulting in image enhancement.

The nature of the interaction between the blocking moiety and the target substance will depend on the target substance to be detected or visualized via MRI. For example, suitable target substances include, but are not limited to, enzymes; proteins; peptides; ions such as Ca+2, Mg+2, Zn+2, Cl−, and Na+; cAMP; receptors such as cell-surface receptors and ligands; hormones; antigens; antibodies; ATP; NADH; NADPH; $FADH_2$; $FNNH_2$; coenzyme A (acyl CoA and acetyl CoA); and biotin, among others.

In some embodiments, the nature of the interaction is irreversible, such that the blocking moiety does not reassociate to block or occupy the coordination site; for example, when the blocking moiety comprises an enzyme substrate which is cleaved upon exposure to the target enzyme. Alternatively, the nature of the interaction is reversible, such that the blocking moiety will reassociate with the complex to hinder the exchange of water; for example, when the blocking moiety comprises an ion ligand, as outlined below.

The corresponding blocking moieties will be enzyme substrates or inhibitors, receptor ligands, antibodies, antigens, ion binding compounds, etc.

In a preferred embodiment, the target substance is an enzyme, and the blocking moiety is an enzyme substrate. In this embodiment, the blocking moiety is cleaved from the metal ion complex of the invention, allowing the exchange of water in at least one coordination site of the metal ion complex. This embodiment allows the amplification of the image enhancement since a single molecule of the target substance is able to generate many activated metal ion complexes, i.e. metal ion complexes in which the blocking moiety is no longer occupying or blocking a coordination site of the metal ion.

As will be appreciated by those skilled in the art, the possible enzyme target substances are quite broad. The target substance enzyme may be chosen on the basis of a correlation to a disease condition, for example, for diagnostic purposes. Alternatively, the metal ion complexes of the present invention may be used to establish such correlations.

Suitable classes of enzymes include, but are not limited to, hydrolases such as proteases, carbohydrases, lipases; isomerases such as racemases, epimerases, tautomerases, or mutases; transferases, kinases and phophatases.

As will be appreciated by those skilled in the art, the potential list of suitable enzyme targets is quite large. Enzymes associated with the generation or maintenance of arterioschlerotic plaques and lesions within the circulatory system, inflammation, wounds, immune response, tumors, may all be detected using the present invention. Enzymes such as lactase, maltase, sucrase or invertase, α-amylase, aldolases, glycogen phosphorylase, kinases such as hexokinase, proteases such as serine, cysteine, aspartyl and metalloproteases may also be detected, including, but not limited to, trypsin, chymotrypsin, and other therapeutically relevant serine proteases such as tPA and the other proteases of the thrombolytic cascade; the cathepsins, including cathepsin B, L, S, H, J, N and O; and calpain. Similarly, bacterial and viral infections may be detected via characteristic bacterial and viral enzymes. As will be appreciated in the art, this list is not meant to be limiting.

Once the target enzyme is identified or chosen, enzyme substrate blocking moieties can be designed using well known parameters of enzyme substrate specificities.

For example, when the enzyme target substance is a protease, the blocking moiety may be a peptide or polypeptide which is capable of being cleaved by the target protease. By "peptide" or "polypeptide" herein is meant a compound of about 2 to about 15 amino acid residues covalently linked by peptide bonds. Preferred embodiments utilize polypeptides from about 2 to about 8 amino acids, with about 2 to about 4 being the most preferred. Preferably, the amino acids are naturally occurring amino acids, although amino acid analogs and peptidomimitic structures are also useful. Under certain circumstances, the peptide may be only a single amino acid residue.

Similarly, when the enzyme target substance is a carbohydrase, the blocking moiety will be a carbohydrate group which is capable of being cleaved by the target carbohydrase. For example, when the enzyme target is lactase or β-galactosidase, the enzyme substrate blocking moiety is lactose or galactose. Similar enzyme/blocking moiety pairs include sucrase/sucrose, maltase/maltose, and α-amylase/amylose.

The blocking moiety itself may block or occupy at least one coordination site of the metal ion. That is, one or more atoms of the enzyme substrate (or, as outlined below, of the moiety which interacts with a physiological agent) itself serves as a coordination atom, or otherwise blocks access to the metal ion by steric hinderance. For example, it appears that one or more of the atoms of the galactose blocking moiety outlined in the Examples may be direct coordination atoms for the Gd(III) metal ion. Similarly, peptide based blocking moieties for protease targets may contribute coordination atoms.

In an alternative embodiment, the blocking moiety further comprises a "coordination site barrier" which is covalently tethered to the complex by one or more enzyme substrate blocking moieties. In this embodiment, the coordination site barrier blocks or occupies at least one of the coordination sites of the metal ion in the absence of the target enzyme substance. Coordination site barriers are used when coordination atoms are not provided by the functional portion of the blocking moiety, i.e. the component of the blocking moiety which interacts with the target substance. The enzyme substrate moiety or moieties serves as the tether, covalently linking the coordination site barrier to the metal ion complex. In the presence of the enzyme target, the enzyme cleaves one or more of the enzyme substrates, either within the substrate or at the point of attachment to the metal ion complex, thus freeing the coordination site barrier. The coordination site or sites are no longer blocked and the bulk water is free to rapidly exchange at the coordination site of the metal ion, thus enhancing the image.

In one embodiment, the coordination site barrier is attached to the metal ion complex at one end, as is depicted in FIG. 1. When the enzyme target cleaves the substrate blocking moiety, the coordination site barrier is completely released. In another embodiment, the coordination site barrier is attached to the metal ion complex with more than one substrate blocking moiety, as is depicted in FIG. 2 for two attachments. The enzyme target may cleave only one side, thus removing the coordination site barrier and allowing the exchange of water at the coordination site, but leaving the coordination site barrier attached to the metal ion complex. Alternatively, the enzyme may cleave the coordination site barrier completely from the metal ion complex.

In a preferred embodiment, the coordination site barrier occupies at least one of the coordination sites of the metal ion. That is, the coordination site barrier contains at least one atom which serves as at least one coordination atom for the metal ion. In this embodiment, the coordination site barrier may be an alkyl amine group, as defined above, including alkyl pyridine, alkyl pyrroline, alkyl pyrrolidine, and alkyl pyrole, or a carboxylic or carbonyl group. The portion of the coordination site barrier which does not contribute the coordination atom may also be consider a linker group. Preferred coordination site barriers are depicted in FIG. 2.

In an alternative embodiment, the coordination site barrier does not directly occupy a coordination site, but instead blocks the site sterically. In this embodiment, the coordination site barrier may be an alkyl or substituted group, as defined above, or other groups such as peptides or proteins.

In this embodiment, the coordination site barrier is preferably linked via two enzyme substrates to opposite sides of the metal ion complex, effectively "stretching" the coordination site barrier over the coordination site or sites of the metal ion complex, as is depicted in FIG. 2.

In some embodiments, the coordination site barrier may be "stretched" via an enzyme substrate on one side, covalently attached to the metal ion complex, and a linker moiety, as defined below, on the other. In an alternative embodiment, the coordination site barrier is linked via a single enzyme substrate on one side; that is, the affinity of the coordination site barrier for the metal ion is higher than that of water, and thus the blocking moiety, comprising the coordination site barrier and the enzyme substrate, will block or occupy the available coordination sites in the absence of the target enzyme.

In another embodiment, the blocking moiety may be an enzyme inhibitor, such that in the presence of the enzyme, the inhibitor blocking moiety disassociates from the metal ion complex to interact or bind to the enzyme, thus freeing an inner coordination sphere site of the metal ion for interaction with water. As above, the enzyme inhibitors are chosen on the basis of the enzyme target substance and the corresponding known characteristics of the enzyme.

In a preferred embodiment, the target substance is a physiological agent. As for the enzyme/substrate embodiment, the physiological agent interacts with the blocking moiety of the metal ion complex, such that in the presence of the physiological agent, there is rapid exchange of water in at least one inner sphere coordination site of the metal ion complex. Thus, the target substance may be a physiologically active ion, and the blocking moiety is an ion binding ligand. For example, as shown in the Examples, the target substance may be the Ca+2 ion, and the blocking moiety may be a calcium binding ligand such as is known in the art (see Grynkiewicz et al., J. Biol. Chem. 260(6):3440–3450 (1985); Haugland, R. P., Molecular Probes Handbook of Fluorescent Probes and Research Chemicals (1989–1991)). Other suitable target ions include Mn+2, Mg+2, Zn+2, Na+, and Cl−.

When Ca+2 is the target substance, preferred blocking moieties include, but are not limited to, the acetic acid groups of bis(o-amino-phenoxy)ethane-N,N,N',N'-tetraacetic acid (BAPTA), ethylene glycol bis(β-aminoethyl ether)-N,N,N',N'-tetraacetic acid (EGTA); ethylenediamine-tetracetic acid (EDTA); and derivatives thereof, such as disclosed in Tsien, Biochem. 19:2396–2404 (1980). Other known chelators of Ca+2 and other divalent ions, such as quin2 (2-[[2-[bis(carboxymethyl)amino]-5-methylphenoxy] methyl-6-methoxy-8-[bis(carboxymethyl)amino]quinoline; fura-1, fura-2, fura-3, stil-1, stil-2 and indo-1 (see Grynkiewicz et al., supra).

As for the enzyme/substrate embodiments, the metabolite may be associated with a particular disease or condition within an animal. For example, as outlined below, BAPTA-DOTA derivatives may be used to diagnose Alzeheimer's disease and other neurological disorders.

In some embodiments, the metal ion complexes of the invention have a single associated or bound blocking moiety. In such embodiments, the single blocking moiety impedes the exchange of water molecules in at least one coordination site. Alternatively, as is outlined below, a single blocking moiety may hinder the exchange of water molecules in more than one coordination site.

In alternative embodiments, two or more blocking moieties are associated with a single metal ion complex, to impede the exchange of water in at least one or more coordination sites.

It should be appreciated that the blocking moieties of the present invention may further comprise a linker group as well as a functional blocking moiety. That is, blocking moieties may comprise functional blocking moieties in combination with a linker group and/or a coordination site barrier.

Linker groups will be used to optimize the steric considerations of the metal ion complex. That is, in order to optimize the interaction of the blocking moiety with the metal ion, linkers may be introduced to allow the functional blocking moiety to block or occupy the coordination site. In general, the linker group is chosen to allow a degree of structural flexibility. For example, when a blocking moiety interacts with a physiological agent which does not result in the blocking moiety being cleaved from the complex, the linker must allow some movement of the blocking moiety away from the complex, such that the exchange of water at at least one coordination site is increased.

Generally, suitable linker groups include, but are not limited to, alkyl groups, as defined above, and alkyl amine groups, as defined above. Preferred linker groups include p-aminobenzyl, substituted p-aminobenzyl, diphenyl and substituted diphenyl, alkyl furan such as benzylfuran, carboxy, and straight chain alkyl groups of 1 to 10 carbons in length. Particularly preferred linkers include p-aminobenzyl, methyl, butyl, pentyl, hexyl, acetic acid, propionic acid, aminobutyl, p-alkyl phenols, 4-alkylimidazole. The selection of the linker group is generally done using well known molecular modeling techniques, to optimize the obstruction of the coordination site or sites of the metal ion.

The blocking moiety is attached to the metal ion complex in a variety of ways. In a preferred embodiment, as noted above, the blocking moiety is attached to the metal ion complex via a linker group. Alternatively, the blocking moiety is attached directly to the metal ion complex; for example, as outlined below, the blocking moiety may be a substituent group on the chelator.

The blocking moieties are chosen and designed using a variety of parameters. In the embodiment which uses a coordination site barrier, i.e. when the functional group of the blocking moiety does not provide a coordination atom, and the coordination site barrier is fastened or secured on two sides, the affinity of the coordination site barrier of the blocking moiety for the metal ion complex need not be great, since it is tethered in place. That is, in this embodiment, the complex is "off" in the absence of the target substance. However, in the embodiment where the blocking moiety is linked to the complex in such a manner as to allow some rotation or flexibility of the blocking moiety, for example, it is linked on one side only, such as the galactose embodiment of the examples, the blocking moiety should be designed such that it occupies the coordination site a majority of the time. Thus, for example, the galactose-DOTA structure of the examples gives roughly a 20% increase in the signal in the presence of galactosidase, thus indicating that the galactose blocking moiety is in equilibrium between blocking or occupying the coordination site and rotating free in solution.

When the blocking moiety is not covalently tethered on two sides, as is depicted in FIG. 1, it should be understood that blocking moieties and coordination site barriers are chosen to maximize three basic interactions that allow the blocking moiety to be sufficiently associated with the complex to hinder the rapid exchange of water in at least one coordination site of the complex. First, there may be electrostatic interactions between the blocking moiety and the metal ion, to allow the blocking moiety to associate with the complex. Secondly, there may be Van der Waals and dipole-dipole interactions. Thirdly, there may be ligand interactions, that is, one or more functionalities of the blocking moiety may serve as coordination atoms for the metal. In addition, linker groups may be chosen to force or favor certain conformations, to drive the equilibrium towards an associated blocking moiety. Similarly, removing degrees of fredom in the molecule may force a particular conformation to prevail. Thus, for example, the addition of alkyl groups, and particularly methyl groups, at positions equivalent to the $R_9$ to $R_{12}$ positions of Structure 6 when the blocking moiety is attached at W, X, Y or Z, can lead the blocking moiety to favor the blocking position. Similar restrictions can be made in the other embodiments, as will be appreciated by those in the art.

Potential blocking moieties may be easily tested to see if they are functional; that is, if they sufficiently occupy or block the appropriate coordination site or sites of the complex to prevent rapid exchange of water. Thus, for example, complexes are made with potential blocking moieties and then compared with the chelator without the blocking moiety in imaging experiments. Once it is shown that the blocking moiety is a sufficient "blocker", the target substance is added and the experiments repeated, to show that interaction with the target substance increases the exchange of water and thus enhances the image.

Thus, as outlined above, the metal ion complexes of the present invention comprise a paramagnetic metal ion bound to a chelator and at least one blocking moiety. In a preferred embodiment, the metal ion complexes have the formula shown in Structure 6:

Structure 6

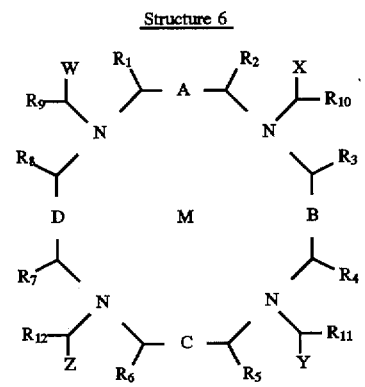

In this embodiment, M is a paramagnetic metal ion selected from the group consisting of Gd(III), Fe(III), Mn(II), Yt(III), and Dy(III). A, B, C and D are each either single or double bonds. The $R_1$ through $R_{12}$ groups are alkyl groups, as defined above, substituted alkyl groups, phosphorus groups, or a blocking moiety, as described above. At least one of the $R_1$ to $R_{12}$ groups are a blocking moiety.

Any or all of A, B, C or D may be a single bond or a double bond. It is to be understood that when one or more of these bonds are double bonds, there may be only a single substituent group attached to the carbons of the double bond. For example, when A is a double bond, there may be only a single $R_1$ and a single $R_2$ group attached to the respective carbons; in a preferred embodiment, as described below, the $R_1$ and $R_2$ groups are hydrogen. In a preferred embodiment, A is a single bond, and it is possible to have two $R_1$ groups and two $R_2$ groups on the respective carbons. In a preferred embodiment, these groups are all hydrogen with the exception of a single blocking moiety, but alternate embodiments utilize two R groups which may be the same or different. That is, there may be a hydrogen and a blocking group attached in the $R_1$ position, and two hydrogens, two alkyl groups, or a hydrogen and an alkyl group in the $R_2$ positions.

It is to be understood that the exact composition of the W, X, Y and Z groups will depend on the presence of the metal ion. That is, in the absence of the metal ion, W, X, Y and Z are —OH, —COOH, $CH_2OH$ or $CH_2COOH$; however, when the metal is present, the groups may be —OH, —COO—, $CH_2OH$ or $CH_2COO$—.

As applied to DOTA, the four nitrogens of the DOTA ring, and the W, X, Y and Z groups provide 8 of the coordination atoms for the paramagnetic metal ion. The ninth coordination atom is provided by a blocking moiety which is substituted at one of the $R_1$ to $R_{12}$ positions. In a preferred embodiment, the other R groups are either hydrogen or methyl; in a particularly preferred embodiment the chelator is Gd-MCTA, which has a single methyl group on the DOTA ring (see Meyer et al., Invest. Radiol. 25:S53 (1990)).

In a preferred embodiment, the compositions have the formula shown in Structure 7:

Structure 7

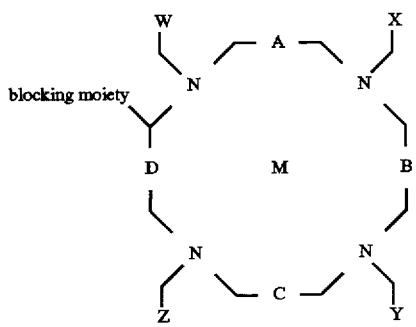

In this embodiment, there is a single blocking moiety attached to the metal ion complex. That is, all but one of the R groups are hydrogen. It should be appreciated that the blocking moiety may be at any of the R positions.

In a preferred embodiment, the magnetic resonance imaging agents are used to detect Ca+2 ions, and have the structure shown below:

Structure 8

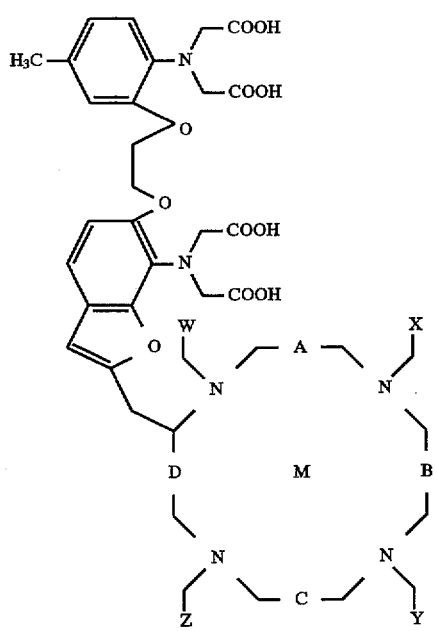

In this embodiment, the blocking moiety comprises a linker and the BAPTA molecule, although any of the fura-type Ca+2 ligands may be substituted. Without being bound by theory, it appears that one of the carboxy groups of the BAPTA moiety serves to provide a coordination atom in the absence of Ca+2. However, in the presence of Ca+2, the carboxy group chelates Ca+2, and thus is unavailable as a coordination group, thus allowing the rapid exchange of water. Preferably, the metal ion is Gd(III), the R groups are all hydrogen, and the W, X, Y and Z groups are carboxy.

In another embodiment, the metal ion complexes have the formula depicted in Structure 9:

Structure 9

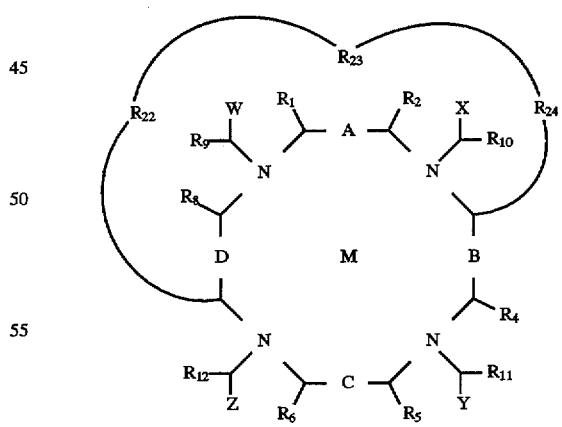

In this embodiment, $R_{22}$, $R_{23}$ and $R_{24}$ comprise a blocking moiety, with $R_{23}$ being a coordination site barrier which also serves to contribute a coordination atom. It is to be understood that the $R_{22}$ and $R_{24}$ groups may be attached at any of the $R_1$ to $R_{12}$ positions. Preferred $R_{23}$ groups include, but are not limited to, compounds listed above and those shown in FIG. 2. $R_{22}$ and $R_{24}$ may also comprise a linker, as defined above and as shown in Structure 10, below. Preferred $R_{22}$ and $R_{24}$ groups include enzyme substrates which are cleaved upon exposure to the enzyme, such as carbohydrates and peptides. Accordingly, when the target substance is a carbohydrase such as β-galactosidase, the compositions have the formula shown in Structure 10:

Structure 10

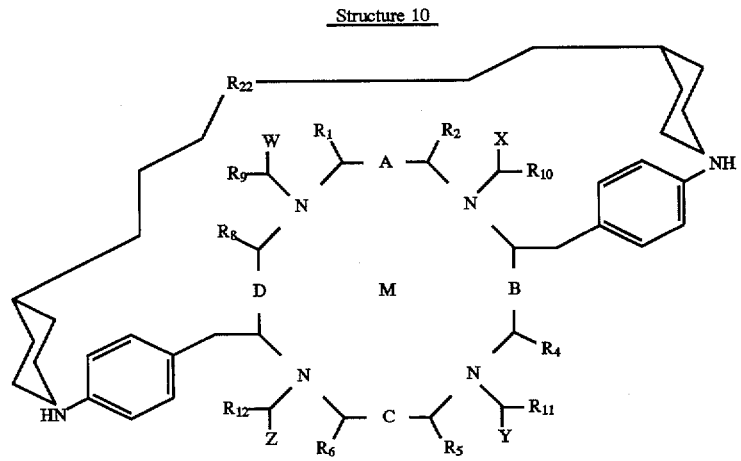

In this embodiment, the blocking moiety comprises two linkers, two carbohydrates, and a coordination site barrier. The carbohydrates are attached to the complex via a linkage which will be recognized by a carbohydrase such as a β(1, 4) linkage such as is recognized by lactose or β-galactosidase. The $R_{22}$ group provides a coordination atom in the absence of the carbohydrase such there is no rapid exchange of water in the complex. Upon exposure to the carbohydrase, such as β-galactosidase, one or both of the carbohydrate blocking moieties are cleaved off, removing the coordination atom and allowing the rapid exchange of water. Preferably, the R groups are hydrogen, and the W, X, Y and Z groups are carboxy. Alternatively, the blocking moiety could comprise peptides for a protease target substance.

In place of the carbohydrates in Structure 10, an alternative embodiment utilizes peptides. That is, a peptide comprising 2 to 5 amino acids or analogs may be "stretched" from one side of the complex to the other, and linker groups may or may not be used.

In an alternative embodiment, the metal ion complexes have the formula depicted in Structure 11:

Structure 11

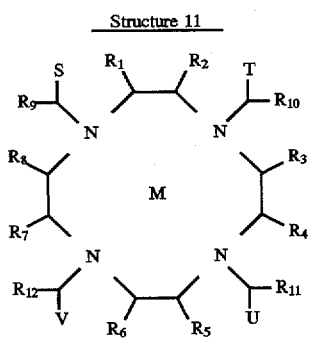

S, T, U, and V are —OH, —COO—, $CH_2OH$, $CH_2COO$—, or a blocking moiety. In this embodiment, the four nitrogens of the DOTA ring, and three of the S, T, U or V groups provide 7 of the coordination atoms for the paramagnetic metal ion. The remaining coordination atoms are provided by a blocking moiety which is substituted at one of the S, T, U or V positions. Alternatively, the coordination sites are either filled by coordination atoms provided by the S, T, U or V groups, or blocked by the S, T, U or V structure, or both.

In a preferred embodiment, the compositions have the formula shown in Structure 12:

Structure 12

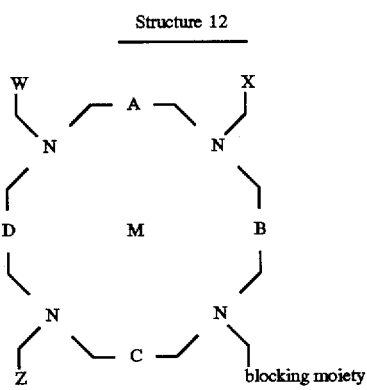

In this embodiment, there is a single blocking moiety attached to the metal ion complex. It should be appreciated that the blocking moiety may be at any of the S, T, U or V positions. Similarly, a single blocking moiety may be attached to DTPA.

In a preferred embodiment, the magnetic resonance imaging contrast agents have the structure shown in Structure 13:

Structure 13

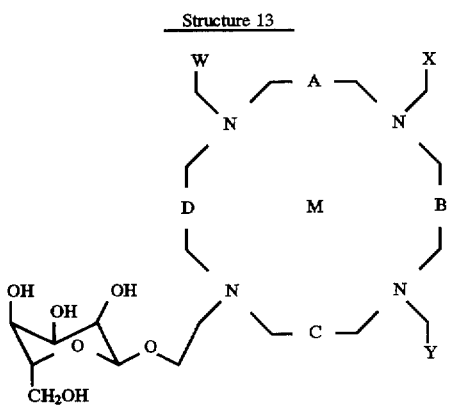

In this embodiment, the blocking moiety comprises a linker and a carbohydrate, attached to the complex via a β(1, 4) linkage such as is recognized by lactose or β-galactosidase. Without being bound by theory, it appears that the galactose moiety provides a coordination atom, such that in the absence of β-galactosidase there is no rapid exchange of water in the complex. Upon exposure to β-galactosidase, the carbohydrate blocking moiety is cleaved off, removing the coordination atom and allowing the rapid exchange of water. Preferably, the R groups are hydrogen, and the W, X, Y and Z groups are carboxy.

A further embodiment utilizes metal ion complexes having the formula shown in Structure 14:

Structure 14

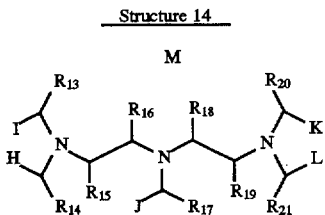

It is to be understood that, as above, the exact composition of the H, I, J, K and L groups will depend on the presence of the metal ion. That is, in the absence of the metal ion, H, I, J, K and L are —OH, —COOH, $CH_2OH$ or $CH_2COOH$; however, when the metal is present, the groups are —OH, —COO—, $CH_2OH$ or $CH_2COO$—.

In this embodiment, $R_{13}$ through $R_{21}$ are alkyl, substituted alkyl, a phosphorus moiety or a blocking moiety, all as defined above. In a preferred embodiment, $R_{12}$ to $R_{21}$ are hydrogen. At least one of $R_{13}$–$R_{21}$, H, I, J, K or L is a blocking moiety, as defined above.

In addition, the complexes and metal ion complexes of the invention further comprise one or more targeting moieties. That is, a targeting moiety may be attached at any of the R positions, although in a preferred embodiment the targeting moiety does not replace a coordination atom. By "targeting moiety" herein is meant a functional group which serves to target or direct the complex to a particular location or association. Thus, for example, antibodies, cell surface receptor ligands and hormones, lipids, sugars and dextrans, alcohols, bile acids, fatty acids, amino acids, and peptides may all be attached to localize or target the contrast agent to a particular site.

In a preferred embodiment, the metal ion complexes of the present invention are water soluble or soluble in aqueous solution. By "soluble in aqueous solution" herein is meant that the MRI agent has appreciable solubility in aqueous solution and other physiological buffers and solutions. Solubility may be measured in a variety of ways. In one embodiment, solubility is measured using the United States Pharmacopeia solubility classifications, with the metal ion complex being either very soluble (requiring less than one part of solvent for 1 part of solute), freely soluble (requiring one to ten parts solvent per 1 part solute), soluble (requiring ten to thirty parts solvent per 1 part solute), sparingly soluble (requiring 30 to 100 parts solvent per 1 part solute), or slightly soluble (requiring 100–1000 parts solvent per 1 part solute).

Testing whether a particular metal ion complex is soluble in aqueous solution is routine, as will be appreciated by those in the art. For example, the parts of solvent required to solubilize a single part of MRI agent may be measured, or solubility in gm/ml may be determined.

The complexes of the invention are generally synthesized using well known techniques. See, for example, Moi et al., supra; Tsien et al., supra; Borch et al., J. Am. Chem. Soc., p2987 (1971); Alexander, (1995), supra; Jackels (1990), supra, U.S. Pat. Nos. 5,155,215, 5,087,440, 5,219,553, 5,188,816, 4,885,363, 5,358,704, 5,262,532; Meyer et al., (1990), supra, Moi et al., (1988), and McMurray et al., Bioconjugate Chem. 3(2):108–117 (1992)).

For DOTA derivatives, the synthesis depends on whether nitrogen substitution or carbon substitution of the cyclen ring backbone is desired. For nitrogen substitution, such as is exemplified by the galactose-DOTA structures of the examples, the synthesis begins with cyclen or cyclen derivatives, as is well known in the art; see for example U.S. Pat. Nos. 4,885,363 and 5,358,704. FIGS. 3 and 4 depict the nitrogen substitution as exemplified by galactose-DOTA derivatives.

For carbon substitution, such as is exemplified by the BAPTA-DOTA structures of the examples, well known techniques are used. See for example Moi et al., supra, and Gansow, supra. FIGS. 5 and 6 depict the carbon substitution as exemplified by the BAPTA-DOTA type derivatives.

The contrast agents of the invention are complexed with the appropriate metal ion as is known in the art. While the structures depicted herein all comprise a metal ion, it is to be understood that the contrast agents of the invention need not have a metal ion present initially. Metal ions can be added to water in the form of an oxide or in the form of a halide and treated with an equimolar amount of a contrast agent composition. The contrast agent may be added as an aqueous solution or suspension. Dilute acid or base can be added if need to maintain a neutral pH. Heating at temperatures as high as 100° C. may be required.

The complexes of the invention can be isolated and purified, for example using HPLC systems.

Pharmaceutical compositions comprising pharmaceutically acceptable salts of the contrast agents can also be prepared by using a base to neutralize the complexes while they are still in solution. Some of the complexes are formally uncharged and do not need counterions.

Once synthesized, the metal ion complexes of the invention have use as magnetic resonance imaging contrast or enhancement agents. Specifically, the functional MRI agents of the invention have several important uses. First, they may be used to diagnose disease states of the brain, as is outlined below. Second, they may be used in real-time detection and differentiation of myocardial infraction versus ischemia. Third, they may be used in in vivo, i.e. whole organism, investigation of antigens and immunocytochemistry for the location of tumors. Fourth, they may be used in the identification and localization of toxin and drug binding sites. In addition, they may be used to perform rapid screens of the physiological response to drug therapy.

The metal ion complexes of the invention may be used in a similar manner to the known gadolinium MRI agents. See for example, Meyer et al., supra; U.S. Pat. No. 5,155,215; U.S. Pat. No. 5,087,440; Margerstadt et al., Magn. Reson. Med. 3:808 (1986); Runge et al., Radiology 166:835 (1988); and Bousquet et al., Radiology 166:693 (1988). The metal ion complexes are administered to a cell, tissue or patient as is known in the art. A "patient" for the purposes of the present invention includes both humans and other animals and organisms, such as experimental animals. Thus the methods are applicable to both human therapy and veterinary applications. In addition, the metal ion complexes of the invention may be used to image tissues or cells; for example, see Aguayo et al., Nature 322:190 (1986).

Generally, sterile aqueous solutions of the contrast agent complexes of the invention are administered to a patient in a variety of ways, including orally, intrathecally and especially intraveneously in concentrations of 0.003 to 1.0 molar, with dosages from 0.03, 0.05, 0.1, 0.2, and 0.3 millimoles per kilogram of body weight being preferred. Dosages may depend on the structures to be imaged. Suitable dosage levels for similar complexes are outlined in U.S. Pat. Nos. 4,885,363 and 5,358,704.

In addition, the contrast agents of the invention may be delivered via specialized delivery systems, for example, within liposomes (see Navon, Magn. Reson. Med. 3:876–880 (1986)) or microspheres, which may be selectively taken up by different organs (see U.S. Pat. No. 5,155,215).

In some embodiments, it may be desirable to increase the blood clearance times (or half-life) of the MRI agents of the invention. This has been done, for example, by adding carbohydrate polymers to the chelator (see U.S. Pat. No. 5,155,215). Thus, one embodiment utilizes polysaccharides as substitution R groups on the compositions of the invention.

A preferred embodiment utilizes complexes which cross the blood-brain barrier. Thus, as is known in the art, a DOTA derivative which has one of the carboxylic acids replaced by an alcohol to form a neutral DOTA derivative has been shown to cross the blood-brain barrier. Thus, for example, neutral complexes are designed that cross the blood-brain barrier with blocking moieties which detect Ca+2 ions. These compounds are used in MRI of a variety of neurological disorders, including Alzeheimer's disease. Currently it is difficult to correctly diagnosis Alzeheimer's disease, and it would be useful to be able to have a physiological basis to distinguish Alzeheimer's disease from depression, or other treatable clinical symptoms for example.

The following examples serve to more fully describe the manner of using the above-described invention, as well as to set forth the best modes contemplated for carrying out various aspects of the invention. It is understood that these examples in no way serve to limit the true scope of this invention, but rather are presented for illustrative purposes. The references cited herein are expressly incorporated by reference.

EXAMPLES

Example 1

Synthesis and Characterization of Galactose-DOTA derivative Synthesis of Do3a-hydroxyethyl-beta-galactose Gadolinium complex: The synthesis is outlined in FIGS. 3 and 4. Acetyl protected bromo-galactose (Aldrich) was reacted with homoethanol. Difference ratios of the alpha- and beta-bromoethyl ether of the acetylgalactose were obtained in good yield. The isomers were separated using silica gel chromatography and their assignments were made by hydrolyzing the acetyl protecting groups and comparing the proton NMR coupling constants to known compounds. Recently an x-ray structure was done confirming these assignments (data not shown).

The beta-isomer was reacted with cyclen at reflux in chloroform with monitoring of the reaction by TLC. Hydrolysis of the acetates was achieved with TEA/McoH/$H_2O$ overnight, and the solvent was removed under low vacuum. The resulting product was reacted directly with bromoacetic acid and then maintained at pH 10–10.5 until the pH remained constant. The possible products all would have different charges in ammonia acetate buffer and thus were separated by anion exchange chromatography. An ammonium acetate buffer gradient was used during FPLC anion exchange to elute the desired compound, with detection at 218 nm. Gadolinium oxide in water at 80° C. was used to insert the metal into the complex. The reaction was followed using fluorescence spectroscopy. The product was purified by HPLC reverse phase chromatography using fluorescence spectroscopy for detection and the structure was confirmed using high resolution mass spectrometry. The overall yield for this essentially one pot synthesis was greater than 25%.

Enzymatic cleavage of the complex: Beta-galactosidase from *E. coli* (Sigma) was added to the Gd complex or first heat inactivated to serve as a control. The incubation was done at 38° C. and the cleavage followed by reverse phase HPLC and TLC which allowed the detection of the newly formed gadolinium complex and reverse phase TLC to detect the free galactose. The $T_1$ change was monitored by NMR, and $T_1$ measured using inversion recovery technique. 180°-tau-90° was the pulse sequence used. There was a 20% increase in the signal using the active enzyme as compared to the heat inactivated enzyme.

Alternate synthetic route: Do3a methyl ester was synthesized by literature methods. Do3a methyl ester was reacted with beta-bromoethyl ether of the acetylgalactose obtained as described in D2O/d4 methanol while maintaining the reaction at basic pH. The reaction was followed by NMR. First the acetate methyl ester cleaved and the sugar became water soluble as judged by allowing the methanol to evaporate. Next the methyl ester was absorbed to cleave and finally at around pH 10 a shift consistant with the formation of the sugar Do3a was observed.

Summary of the synthesis of Do2a-hydroxyethyl-di-beta-galactose: The reaction of cyclen with beta-bromoethyl ether of the acetylgalactose in chloroform was done. The reaction mixture was purified using silica gel chromatography. While the alpha isomer gave monosubstitution only di-substituted products were obtained for the beta isomer as shown in FIG. 5. The acetic acid derived arm was added as described for the monosubstituted compound above and purified by FPLC cation exchange using an acid water gradient. Individual fractions were detected by TLC spotting.

Example 2

Synthesis of BAPTA-DTPA and BAPTA-DOTA derivatives

Two representative synthetic schemes are shown for the synthesis of a BAPTA-DTPA derivative in FIGS. 7 and 8. In FIG. 7, structure I was prepared by modification of published procedures (Tsien et al., supra) and coupled to hexamethylenediamine using $NaCNBrH_3$ in dry methanol. The ratio of reactants used was 6:1:0.6 (diamine:BAPTA aldehyde:$NaCNBrH_3$). The reaction was quenched with the addition of concentrated HCl and the product purified by HPLC (II). This material was reacted with the mon (or bis) anhydride of DTPA with the protecting groups left on the BAPTA until after the Gd(III)Cl$_3$ or Gd$_2$O$_3$ was added (elevated pH, heat). The final product was purified by ion-exchange HPLC.

In FIG. 8, the monoanhydride of DTPA was prepared and reacted with a bisalkylamine (e.g. $NH_2(CH_2)_6(NH_2)$). This material was purified by ion-exchange HPLC and placed in a round bottom flask equipped with argon inlet and pressure equalizing funnel. The BAPTA aldehyde in dry methanol was added dropwise to a solution of alkylamine-DTPA in dry methanol and 6 equivalents of HCl:MeOH was added. The reaction mixture was purified by HPLC, Gd(III) inserted as above, and the protecting groups removed by literature procedures.

We claim:

1. A MRI agent comprising a paramagnetic metal ion bound to a complex, said complex comprising:
   a) a chelator; and
   b) a blocking moiety covalently attached to said chelator which binds in at least a first coordination site of said metal ion and which is capable of interacting with a target substance such that the exchange of water in at least said first coordination site is increased.

2. A MRI agent according to claim 1 wherein said chelator is DOTA.

3. A MRI agent according to claim 1 wherein said chelator is DPTA.

4. A MRI agent according to claim 1 wherein said paramagnetic metal ion is selected from the group consisting of Gd(III), Fe(III), Mn(II), Yt(III), Cr(III) or Dy(III).

5. A MRI agent according to claim 1 wherein said paramagnetic metal ion is Gd(III).

6. A MRI agent comprising
   a) a paramagnetic metal ion capable of binding n coordination atoms, wherein said metal ion is bound to a chelator such that said metal ion has coordination atoms at (n-1) or (n-2) coordination sites of said metal ion; and
   b) a blocking moiety covalently attached to said chelator that hinders the rapid exchange of water in the remaining coordination site or sites,
   wherein said blocking moiety is capable of interacting with a target substance, such that the exchange of water at the remaining coordination site or sites is increased.

7. A MRI agent according to claim 6 comprising
   a) a Gd(III) ion with coordination atoms at 8 coordination sites of said Gd(III) ion; and
   b) a blocking moiety which hinders the rapid exchange of water in a 9th coordination site,
   wherein said blocking moiety is capable of interacting with a target substance, such that the exchange of water at the 9th coordination site is increased.

8. A MRI agent according to claim 6 comprising a Gd(III) ion bound to a chelator with 8 coordination atoms.

9. A MRI agent having the formula comprising:

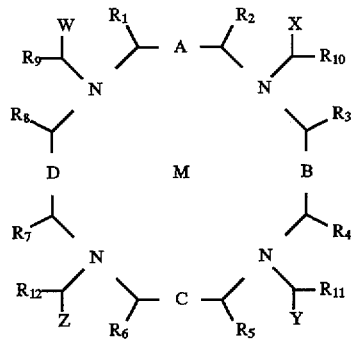

wherein

M is a paramagnetic metal ion selected from the group consisting of Gd(III), Fe(III), Mn(II), Yt(III), Cr(III) and Dy(III);

A, B, C and D are either single bonds or double bonds;

W, X, Y and Z are —OH, —COO—, —CH$_2$OH or —CH$_2$COO—;

$R_1$–$R_{12}$ are hydrogen, alkyl, substituted alkyl, phosphorus moiety, or a blocking moiety;

wherein at least one of $R_1$–$R_{12}$ is a blocking moiety.

10. An MRI agent according to claim 9 having the formula comprising:

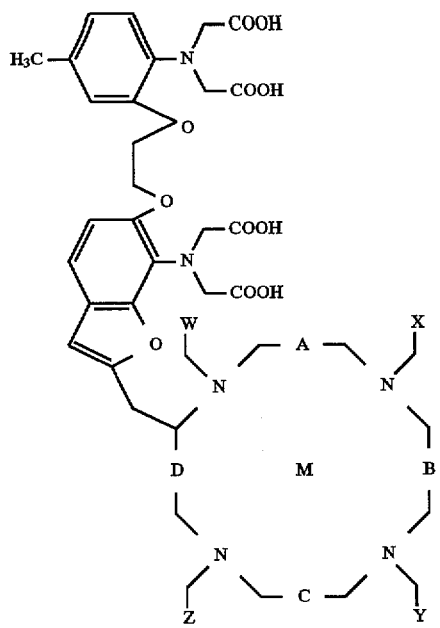

wherein

M is a paramagnetic metal ion selected from the group consisting of Gd(III), Fe(III), Mn(II), Yt(III), Cr(III) and Dy(III);

A, B, C and D are either single bonds or double bonds;

W, X, Y and Z are —OH, —COO—, —CH$_2$OH or —CH$_2$COO—; and $R_1$–$R_{12}$ are hydrogen, alkyl, substituted alkyl, or phosphorus moiety.

11. A MRI agent having the formula comprising:

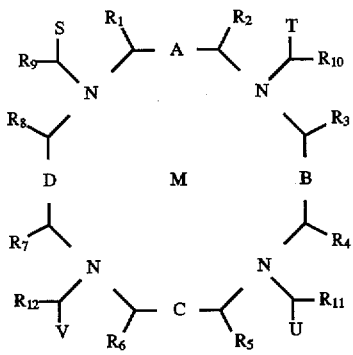

wherein
  M is a paramagnetic metal ion selected from the group consisting of Gd(III), Fe(III), Mn(II), Yt(III), Cr(III) and Dy(III);
  A, B, C, and D are either single or double bonds;
  S, T, U and V are —OH, —COO—, —CH2OH, —CH2COO—, or a blocking moiety;
  $R_1$–$R_{12}$ are hydrogen, alkyl, substituted alkyl, or phosphorus moiety;
  wherein at least one of S, T, U or V is a blocking moiety.

12. An MRI agent according to claim 11 having the formula comprising:

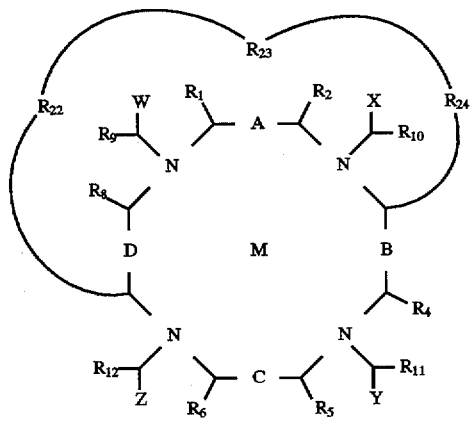

wherein
  M is a paramagnetic metal ion selected from the group consisting of Gd(III), Fe(III), Mn(II), Yt(III), Cr(III) and Dy(III);
  A, B, C and D are either single bonds or double bonds;
  W, X, Y and Z are —OH, —COO—, —$CH_2$OH or —$CH_2$COO—; and
  $R_1$–$R_{12}$ are hydrogen, alkyl, substituted alkyl, phosphorus moiety or a blocking moiety; and
  $R_{22}$, $R_{23}$ and $R_{24}$ comprise a blocking moiety, with $R_{23}$ being a coordination site barrier.

13. An MRI agent according to claim 11 having the formula comprising:

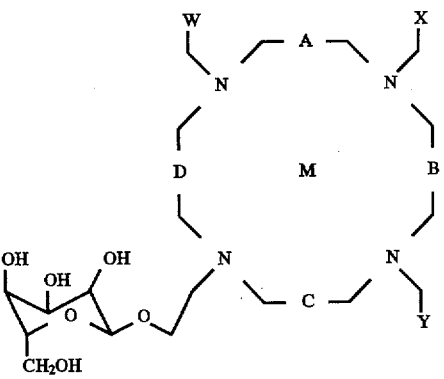

wherein
  M is a paramagnetic metal ion selected from the group consisting of Gd(III), Fe(III), Mn(II), Yt(III), Dy(III), and Cr(III);
  A, B, C and D are either single bonds or double bonds;
  W, X, and Y are —OH, —COO—, —$CH_2$OH or —$CH_2$COO—; and
  $R_1$–$R_{12}$ are hydrogen, alkyl, substituted alkyl, or phosphorus moiety.

14. A MRI agent having the formula comprising:

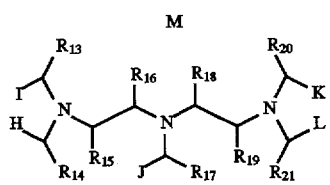

wherein
  M is a paramagnetic metal ion selected from the group consisting of Gd(III), Fe(III), Mn(II), Yt(III), Cr(III) or Dy(III);
  H, I, J, K and L are —OH, —COO—, —CH2OH, —CH2COO—, or a blocking moiety;
  $R_{13}$–$R_{21}$ are hydrogen, alkyl, substituted alkyl, phosphorus moiety or a blocking moiety;
  wherein at least one of $R_{13}$–$R_{21}$, H, I, J, K or L is a blocking moiety.

15. A MRI agent according to claim 9, 11, 12 or 14 wherein said blocking moiety comprises an enzyme substrate.

16. A method of magnetic resonance imaging of a cell, tissue or patient comprising administering an MRI agent according to claim 1 to a cell, tissue or patient and rendering a magnetic resonance image of said cell, tissue or patient.

* * * * *

UNITED STATES PATENT AND TRADEMARK OFFICE
CERTIFICATE OF CORRECTION

PATENT NO. : 5,707,605

DATED : January 13, 1998

INVENTOR(S) : MEADE et al.

It is certified that error appears in the above-indentified patent and that said Letters Patent is hereby corrected as shown below:

Column 1, line 13, immediately preceding BACKGROUND OF THE INVENTION, insert a new paragraph to read --This invention was made with Government support under Grant No. AR-42671, awarded by the National Institutes of Health. The Government has certain rights in the invention.--.

Column 26, line 5, immediately following "derivative" begin a new paragraph.

Signed and Sealed this

Eighteenth Day of August, 1998

Attest:

BRUCE LEHMAN

Attesting Officer

Commissioner of Patents and Trademarks